United States Patent
Wu et al.

(10) Patent No.: US 9,352,024 B2
(45) Date of Patent: May 31, 2016

(54) USES OF INTERLEUKIN-22(IL-22) IN TREATING AND PREVENTING NERVE DAMAGE DISEASES OR NEURODEGENERATIVE DISEASES

(71) Applicant: Generon (Shanghai) Corporation, LTD.

(72) Inventors: Dongdong Wu, Shanghai (CN); Zhihua Huang, Shanghai (CN); Heng Liu, Shanghai (CN); Yuliang Huang, Shanghai (CN); Xiaoqiang Yan, Shanghai (CN)

(73) Assignee: Generon (Shanghai) Corporation LTD., Shanghai (CN)

( * ) Notice: Subject to any disclaimer, the term of this patent is extended or adjusted under 35 U.S.C. 154(b) by 0 days.

(21) Appl. No.: 14/369,187

(22) PCT Filed: Dec. 27, 2012

(86) PCT No.: PCT/CN2012/087694
§ 371 (c)(1),
(2) Date: Jun. 26, 2014

(87) PCT Pub. No.: WO2013/097748
PCT Pub. Date: Jul. 4, 2013

(65) Prior Publication Data
US 2015/0147293 A1    May 28, 2015

(30) Foreign Application Priority Data
Dec. 27, 2011  (CN) .......................... 2011 1 0446936

(51) Int. Cl.
*A61K 38/20* (2006.01)
*A61K 47/48* (2006.01)

(52) U.S. Cl.
CPC ............... *A61K 38/20* (2013.01); *A61K 47/481* (2013.01); *A61K 47/48423* (2013.01)

(58) Field of Classification Search
None
See application file for complete search history.

(56) References Cited

U.S. PATENT DOCUMENTS

| | | |
|---|---|---|
| 6,274,710 B1 | 8/2001 | Dumoutier et al. |
| 6,331,613 B1 | 12/2001 | Dumoutier et al. |
| 6,359,117 B1 | 3/2002 | Dumoutier et al. |
| 6,551,799 B2 | 4/2003 | Gurney et al. |
| 6,797,493 B2 | 9/2004 | Sun et al. |
| 7,307,161 B1 | 12/2007 | Jacobs et al. |
| 7,459,533 B2 | 12/2008 | Jacobs et al. |
| 7,585,646 B2 | 9/2009 | Jacobs et al. |
| 7,666,402 B2 | 2/2010 | Huang et al. |
| 7,696,158 B2 | 4/2010 | Huang et al. |
| 7,718,604 B2 | 5/2010 | Huang et al. |
| 7,972,833 B2 | 7/2011 | Dumoutier et al. |
| 8,048,984 B2 | 11/2011 | Jacobs et al. |
| 8,945,528 B2 | 2/2015 | Yan et al. |
| 2007/0207943 A1* | 9/2007 | Ebner et al. ................ 514/2 |
| 2009/0202475 A1 | 8/2009 | Abbas et al. |
| 2011/0262385 A1 | 10/2011 | Huang et al. |
| 2011/0280828 A1 | 11/2011 | Abbas et al. |
| 2015/0202267 A1 | 7/2015 | Yan et al. |

FOREIGN PATENT DOCUMENTS

| | | |
|---|---|---|
| CN | 101168049 A | 4/2008 |
| CN | 101218254 A | 7/2008 |
| CN | 101225110 A | 7/2008 |
| CN | 102380091 A | 3/2012 |
| JP | 2008-508862 A | 3/2008 |
| WO | WO-99/61617 A1 | 12/1999 |
| WO | WO-02/29098 A2 | 4/2002 |
| WO | WO-2006/000448 A2 | 1/2006 |
| WO | WO-2006/088833 A2 | 8/2006 |
| WO | WO-2011/087986 A1 | 7/2011 |
| WO | WO-2012/028089 A1 | 3/2012 |

OTHER PUBLICATIONS

Zenewicz et al., Recent advances in IL-22 biology, 2011, International Immunology, vol. 23, No. 3, pp. 159-163.*
Asiedu, C. et al. (2007). "Cloning and Characterization of Recombinant Rhesus Macaque IL-10/Fc(ala-ala) Fusion Protein: A Potential Adjunct for Tolerance Induction Strategies" *Cytokine* 40:183-192.
Cox, G.N. et al. (2004). "Enhanced Circulating Half-Life and Hematopoietic Properties of a Human Granulocyte Colony-Stimulating Factor/Immunoglobulin Fusion Protein," *Exp. Hematol.* 32:441-449.
De Oliveira Neto, M. et al. (Mar. 1, 2008; e-pub. Nov. 16, 2007). "Interleukin-22 Forms Dimers That are Recognized by Two Interleukin-22R1 Receptor Chains," *Biophys. J.* 94(5):1754-1765.
Dumoutier, L. et al. (Feb. 15, 2000). "Cloning and Characterization of IL-10-Related T Cell-Derived Inducible Factor (IL-TIF), a Novel Cytokine Structurally Related to IL-10 and Inducible by IL-9," *J. Immunol.* 164(4):1814-1819.
Dumoutier, L. et al. (Aug. 29, 2000). "Human Interleukin-10-related T Cell-Derived Inducible Factor: Molecular Cloning and Functional Characterization as an Hepatocyte-Stimulating Factor," *PNAS* 97(18):10144-10149.
Extended European Search Report mailed on Oct. 10, 2014, for EP Patent Application No. 11821115.0, filed on Aug. 30, 2011, five pages.

(Continued)

*Primary Examiner* — John Ulm
(74) *Attorney, Agent, or Firm* — Morrison & Foerster LLP

(57) ABSTRACT

This invention discloses the uses of IL-22 in the treatment and prevention of a nerve damage disease or a neurodegenerative disease. In particular, the invention discloses the uses of IL-22 or IL-22 dimers as follows: (i) can protect neurons to recover the functions of injured neurons after ischemic nerve damage in animals in vivo, thus enabling effective treatment of nerve damage diseases, (ii) can significantly inhibit the loss of dopaminergic neurons in substantia nigra in PD model animal, enhance the functions of dopaminergic neurons, significantly reduce neuronal apoptosis in hippocampus, improve learning and memory capacity of AD model rats, and effectively prevent neuronal loss, thereby enabling more effective treatment of neurodegenerative diseases.

18 Claims, 5 Drawing Sheets

(56) References Cited

OTHER PUBLICATIONS

Gao, B. (Apr. 2005). "Cytokines, STATs and Liver Disease," *Cell. Mol. Immunol.* 2(2):92-100.

International Search Report mailed on Dec. 8, 2011 for PCT Patent Application No. PCT/CN2011/079124, filed on Aug. 30, 2011, four pages.

International Search Report mailed on Apr. 18, 2013, for PCT Patent Application No. PCT/CN2012/087694, filed on Dec. 27, 2012, four pages.

Kotenko, S.V. et al. (Sep. 8, 1995). "Interaction Between the Components of the Interferon γ Receptor Complex," *J. Biol. Chem.* 270(36):20915-20921.

Li, Q. (Sep. 2003). "Research development of interleukin-22," *Chinese J. of Cancer Biotherapy* 10(3):226-228 (Translation of Abstract Only).

Low, S.C. et al. (Jul. 2005). "Oral and pulmonary delivery of FSH-Fc fusion proteins via neonatal Fc receptor-mediated transcytosis," *Human Reproduction* 20(7):1805-1813.

Pan, H. et al. (Feb. 2004). "Hydrodynamic Gene Delivery of Interleukin-22 Protects the Mouse Liver from Concanavalin A-, Carbon Tetrachloride-, and Fas Ligand-Induced Injury Via Activation of STAT3," *Cell. Mol. Immunol.* 1(1):43-49.

Radaeva, S. et al. (May 2004). "Interleukin 22 (IL-22) Plays a Protective Role in T Cell-Mediated Murine Hepatitis: IL-22 is a Survival Factor for Hepatocytes Via STAT3 Activation," *Hepatology* 39(5):1332-1342.

Wolk, K. et al. (Jun. 1, 2002). "Cutting Edge: Immune Cells as Sources and Targets of the IL-10 Family Members?," *J. Immunol.* 168(11):5397-5402.

Written Opinion of the International Searching Authority mailed on Dec. 8, 2011 for PCT Patent Application No. PCT/CN2011/079124, filed on Aug. 30, 2011, seven pages.

Written Opinion of the International Searching Authority mailed on Apr. 18, 2013, for PCT Patent Application No. PCT/CN2012/087694, filed on Dec. 27, 2012, eleven pages.

Wu, C. et al. (Nov. 2007; e-pub. Oct. 14, 2007). "Simultaneous Targeting of Multiple Disease Mediators by a Dual-Variable-Domain Immunoglobulin," *Nat. Biotechnol.* 25(11):1290-1297.

Xie, M.H. et al. (Oct. 6, 2000; e-pub. Jun. 29, 2000). "Interleukin (IL)-22, a Novel Human Cytokine that Signals Through the Interferon Receptor-Related Proteins CRF2-4 and IL-22R," *J. Biol. Chem.* 275(40):31335-31339.

Zheng, X.X. et al. (1995). "Administration of Noncytolytic IL-10/Fc in Murine Models of Lipopolysaccharide-Induced Septic Shock and Allogeneic Islet Transplantation," *J. Immunol.* 154(10):5590-5600.

Zhu, H. et al. (Nov. 12, 2004). "STAT3 Induces Anti-Hepatitis C Viral Activity in Liver Cells," *Biochem. Biophys. Res. Commun.* 324(2):518-528.

Zhu, Q. et al. (Nov. 2008). "Expression of rhEPO-L-Fc Fusion Protein and Analysis of its Bioactivity and Pharmacokinetics," *Sheng Wu Gong Cheng Xue Bao* 24(11):1874-1879 (English Abstract).

U.S. Appl. No. 12/672,274, filed Aug. 1, 2008, by Huang et al.

Cobleigh, M.A. et al. (Jan. 2013). "Protective and Pathological Properties of IL-22 in Liver Disease: Implications for Viral Hepatitis," *Am. J. Pathology* 182(1):21-28.

Dambacher, J. et al. (Mar. 2008). "The Role of Interleukin-22 in Hepatitis C Virus Infection," *Cytokine* 41(3):209-216.

Eyerich, S. et al. (Sep. 2010; e-pub. Aug. 4, 2010). "IL-17 and IL-22: Siblings, Not Twins," *Trends Immunol.* 31(9):354-361.

Jones, B.C. et al. (Apr. 1, 2008; e-pub. Mar. 21, 2008). "Crystallization and Preliminary X-Ray Diffraction Analysis of Human IL-22 Bound to the Extracellular IL-22R1 Chain," *Acta Crystall. Sect. F. Structure Biol. Cryst. Commun.* 64(Pt. 4):266-269.

Who. (Jul. 2015). "What is Hepatitis?" located at http://www.who.int/features/qa/76/en/, last visited on Jan. 15, 2016, three pages.

\* cited by examiner

Normal control　　　　　　MPTP model

MPTP + IL-22-D 100 μg/kg　　　MPTP + IL-22 40 μg/kg

USES OF INTERLEUKIN-22(IL-22) IN TREATING AND PREVENTING NERVE DAMAGE DISEASES OR NEURODEGENERATIVE DISEASES

CROSS-REFERENCE TO RELATED APPLICATIONS

This application is a National Phase application under 35 U.S.C. §371 of International Application No. PCT/CN2012/087694, filed Dec. 27, 2012 and claims benefit of Chinese Application No. 201110446936.3, filed Dec. 27, 2011, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720622000600SubSeqList.txt, date recorded: Oct. 6, 2014, size: 19 KB).

FIELD OF THE INVENTION

This invention relates to the fields of biology and medicine. In particular, this invention relates to the use of interleukin-22 in the treatment and prevention of nerve damage diseases or neurodegenerative diseases.

BACKGROUND OF INVENTION

Interleukin-22 (IL-22), also known as interleukin-10 related T cell-derived inducible factor (IL-TIF), is a glycoprotein secreted by T cells. The expression of IL-22 mRNA was originally demonstrated in IL-9-stimulated T cell lines, IL-9-stimulated mast cell line, as well as concanavalinA activated spleen cells of mouse. The human IL-22 mRNA is mainly expressed in isolated peripheral T cells and are upon stimulation by anti-CD-3 antibody or ConA. IL-22 mRNA is also expressed in the stimulated NK cells. Activated T cells are mainly CD4+ cells, especially Th1 cells via the CD28 pathway.

IL-22 precursor is composed of 179 amino acid residues (the mature peptide is composed of 146 amino acid residues). Dumoutier et al. first reported the cloned IL-22 genes of mouse and human (Dumoutier, et al., JI 164:1814-1819, 2000). In addition, Dumoutier obtained patents related to IL-22 (U.S. Pat. No. 6,359,117 and U.S. Pat. No. 6,274,710), whereas Gurney obtained a patent related to use of IL-22 in the treatment of human pancreatic disease (U.S. Pat. No. 6,551,799).

IL-22 is mainly expressed in thymus, brain, activated T cells and mast cells, the lectin-stimulated spleen cells (Duroutier JI 2002), interleukin-2/interleukin-12-stimulated NK cells (Wolk, K JI 2002), and in a number of organs and tissues, including gut, liver, stomach, kidney, lung, heart, thymus, and spleen, upon LPS stimulation (Dumoutier PNAS paper), in which an increase of the expression of IL-22 in those organs and tissues can be measured.

IL-22 exerts its biological function by binding IL-22R1 receptor and IL-10R2 receptor. IL-22R1 is a receptor specific to IL-22 and is expressed in skin, kidney, the digestive system (pancreas, small intestine, liver, large intestine, colon), and the respiratory system (lung, bronchi). The research on IL-22 as a regulatory agent to the immune system has been published. The medical use of IL-22 in reducing serum triglycerides and obesity has been reported in patent applications related to the medical uses of IL-22 (See WO 2006/073 508 and CN 200510023103.0). However, it has not yet been discovered that IL-22 can play an active role in the treatment of nerve damage diseases or neurodegenerative diseases.

Neurodegenerative disease is a condition of progressive degeneration and death of neurons in brain and spinal cord. It is a kind of chronic and progressive disease of the nervous system, mainly including Alzheimer's disease (AD), Parkinson's disease (PD), Huntington disease, amyotrophic lateral sclerosis, spinal muscular atrophy, and spinal cerebellar ataxias, etc. These neurological diseases are characterized by a common feature of degeneration and apoptosis of neurons, which result in the abnormal behavior and dysfunction of patients, and lead to a premature death. The pathogenesis of neurodegenerative diseases remains obscure, as yet no existing effective method and medicine are available. Current treatments for PD comprise the replenishment of neurotransmitters in patients' brain via oral administration or intravenous injection, such as levodopa, whereas levodopa cannot effectively control the naturally pathogenic progression of PD and cannot affect the speed of degeneration of dopaminergic neurons. Moreover, long-term use of levodopa brings a variety of adverse side effects, such as on-off phenomenon and dyskinesia, and its therapeutic effects only last about 2 years. Long-term use of levodopa may cause neuronal damage as well as speeding up apoptosis of the neurons. Current treatments for AD comprise increasing the concentration of acetylcholine directed against the deficiency of acetylcholine in AD patients' brain using choline esterase inhibitors. This method is only symptomatic treatment and cannot control the development of the disease, either.

Therefore, there is an urgent need in the art to develop more effective drugs or methods for treatment and prevention of nerve damage diseases or neurodegenerative diseases.

SUMMARY OF INVENTION

It is an object of the present invention to provide an effective drug for the treatment and prevention of nerve damage diseases or neurodegenerative diseases and the use thereof, i.e. the use of interleukin-22 (IL-22) in the treatment and prevention of nerve damage diseases or neurodegenerative diseases in mammals.

In one aspect of the present invention, a use of IL-22 or a dimer or a multimer thereof in the manufacture of a medicament for treatment and prevention of nerve damage diseases or neurodegenerative diseases is provided.

In another preferred embodiment, the nerve damage disease is selected from stroke, spinal injury, and neurological disorders accompanied with blood brain barrier injury.

The neurodegenerative disease is selected from Parkinson's disease, Alzheimer's disease, Huntington disease, amyotrophic lateral sclerosis, spinal muscular atrophy, primary lateral sclerosis, and spinal cerebellar ataxias.

In another preferred embodiment, the IL-22 comprises human IL-22 or mammalian (such as mouse, rabbit, cattle, or sheep) IL-22.

In another preferred embodiment, the IL-22 comprises recombinant IL-22 or natural IL-22.

In another preferred embodiment, the IL-22 dimer is shown as Formula I:

$$M1\text{-}L\text{-}M2 \qquad \qquad I$$

wherein
M1 is a first monomer of IL-22,
M2 is a second monomer of IL-22, and
L is a linker connecting said first monomer and said second monomer and disposed therebetween,
wherein the IL-22 dimer retains the biological activity of IL-22 and has a serum half-life of longer than twice of that of either the first or the second monomer.

In another preferred embodiment, the serum half-life of the IL-22 dimer is longer than three, five, or ten times of that of the first and/or the second monomer.

In an preferred embodiment, the linker L is selected from the group consisting of:
(i). a short peptide comprising 3 to 50 amino acids; and
(ii). a polypeptide of Formula II:

$$-Z-Y-Z-\qquad \text{II}$$

wherein
Y is a carrier protein,
Z is nothing, or a short peptide(s) comprising 1 to 30 amino acids, and
"—" is a chemical bond or a covalent bond.

In another preferred embodiment, the first monomer and the second monomer are identical.

In another preferred embodiment, the first monomer and the second monomer are different.

In another preferred embodiment, the biological activity is selected from one or more activities in a group consisting:
(a) activating STAT3 in neurons in vitro;
(b) protecting neurons and reducing the volume of cerebral infarction after ischemic injury in vivo;
(c) activating STAT3 in dopaminergic neurons or hippocampal neurons in vitro;
(d) significantly inhibiting the loss of dopaminergic neurons in substantia nigra in the animal model of PD in vivo;
(e) significantly reducing the apoptosis of neurons in hippocampus in the animal model of AD in vivo.

In another preferred embodiment, the carrier protein is albumin or Fc fragment of human IgG.

In another preferred embodiment, the carrier protein is formed by the connection of two Fc fragments of IgG via disulfide bond. In another preferred embodiment, the number of said disulfide bond is 2-4.

In another preferred embodiment, the "—" is a peptide bond.

In another preferred embodiment, the IL-22 dimer is a dimer formed by monomers in which the monomer comprises an amino acid sequence selected from SEQ ID NOs: 2-5.

In a second aspect of the present invention, a IL-22 dimer of Formula I is provided:

$$\text{M1-L-M2} \qquad \text{I}$$

Wherein
M1 is a first monomer of IL-22;
M2 is a second monomer of IL-22; and
L is a linker connecting said first monomer and said second monomer and disposed therebetween,
wherein, the IL-22 dimer retains the biological activity of IL-22 and has a serum half-life of longer than twice of that of either the first or the second monomer.

In a third aspect of the present invention, a pharmaceutical composition for treatment or prevention of nerve damage diseases or neurodegenerative diseases is provided, which comprise pharmaceutically acceptable carrier and IL-22 dimer of Formula I:

$$\text{M1-L-M2} \qquad \text{I}$$

Wherein
M1 is a first monomer of IL-22;
M2 is a second monomer of IL-22; and
L is a linker connecting said first monomer and said second monomer and disposed therebetween,
wherein, the IL-22 dimer retains the biological activity of IL-22 and has a serum half-life of longer than twice of that of either the first or the second monomer.

In another preferred embodiment, the IL-22 dimer is a dimer formed by monomers in which the monomer comprises an amino acid sequence selected from SEQ ID NOs: 3 and 5.

In another preferred embodiment, the IL-22 dimer is prepared by following the steps of:
a) transforming mammalian cells with an expression vector comprising a DNA sequence encoding a IL-22-Fc complex;
b) culturing the mammalian cells; and
c) isolating and purifying the IL-22 dimer.

On one hand, the IL-22 dimer molecules of the present invention can protect neurons upon ischemic nerve damage in animal in vivo, thereby enabling recovery of the functions of damaged neurons, and effective treatment of nerve damage diseases. On the other hand, the IL-22 dimer molecules can significantly inhibit the loss of dopaminergic neurons in substantia nigra in the animal model of PD, and enhance the functions of dopaminergic neurons. In addition, the IL-22 dimer molecules can significantly improve learning and memory capacity of AD rat model, protect neurons, reduce neuronal apoptosis in hippocampus, and alleviate the syndromes of dementia. The IL-22 dimer of the present invention has a prolonged half life in serum and is capable of effectively preventing neuronal loss, thereby enabling more effective treatment of neurodegenerative diseases.

It is clear for a skilled person in the art that, the technical features mentioned above and discussed in the examples below of the present invention could be combined with each other to result in a new or preferred technical solution. Hence this invention should not be construed as limited to the embodiments set forth herein.

An amino acid sequence of the IL-22 dimer is shown in SEQ ID NO:1 in which amino acid residues 1-146 represent IL-22, amino acid residues 147-162 represent the linker, and residues 163-308 represent another IL-22.

Figures 2A, 2B:
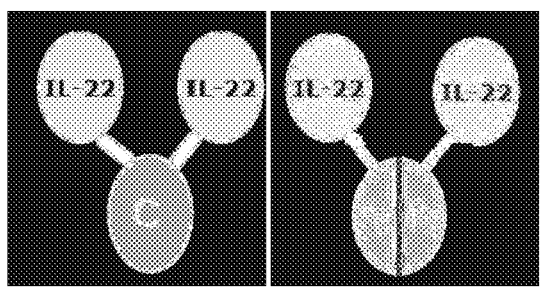

FIGS. 2A and 2B are illustrations of an IL-22 dimer according to the present invention. In the figures, "-" represents an amino acid linker and the oval-shaped object labeled with "IL-22" represents an IL-22 monomer. The oval-shaped object labeled with "C" represents a carrier protein wherein the IL-22 is disposed at the N-terminal of the carrier protein.

An amino acid sequence of an IL-22 monomer with Fc fragment, which is used to form the IL-22 dimer of this embodiment, is shown in SEQ ID NO: 2 in which amino acid residues 1-146 represent an IL-22, amino acid residues 147-162 represent the linker, and residues 163-385 represent Fc fragment of human IgG2. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO: 3 in which amino acid residues 1-146 represent an IL-22, amino acid residues 147-152 represent the linker, and residues 153-375 represent Fc fragment of human IgG2. A dimer is formed by the two IL-22 monomers with Fc fragment via the coupling of the Fc fragments.

Figures 3A, 3B:
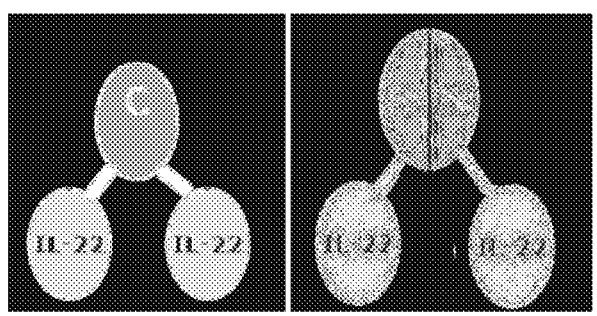

FIGS. 3A and 3B are illustrations of an IL-22 dimer according to the present invention. In the figures, "-" represents an amino acid linker, the oval-shaped object labeled with "IL-22" represents an IL-22 monomer, the oval-shaped object labeled with "C" represents a carrier protein wherein the IL-22 is disposed at the C-terminal of the carrier protein.

An amino acid sequence of an IL-22 monomer with Fc fragment, which is used to form the IL-22 dimer of this embodiment, is shown in SEQ ID NO: 4 in which amino residues 1-223 represent Fc fragment of human IgG2, amino residues 224-239 represent the linker, and residues 240-385 represent an IL-22. A dimer is formed by the two IL-22 monomers with Fc fragment via the coupling of the Fc fragments.

An amino acid sequence of an IL-22 monomer with Fc fragment, which is used to form the IL-22 dimer of this embodiment, is shown in SEQ ID NO:5 in which amino acid residues 1-223 represent Fc fragment of human IgG2, amino acid residues 224-229 represent the linker, and residues 230-375 represent an IL-22. A dimer is formed by the two IL-22 monomers with Fc fragment via the coupling of the Fc fragments.

Figure 4:
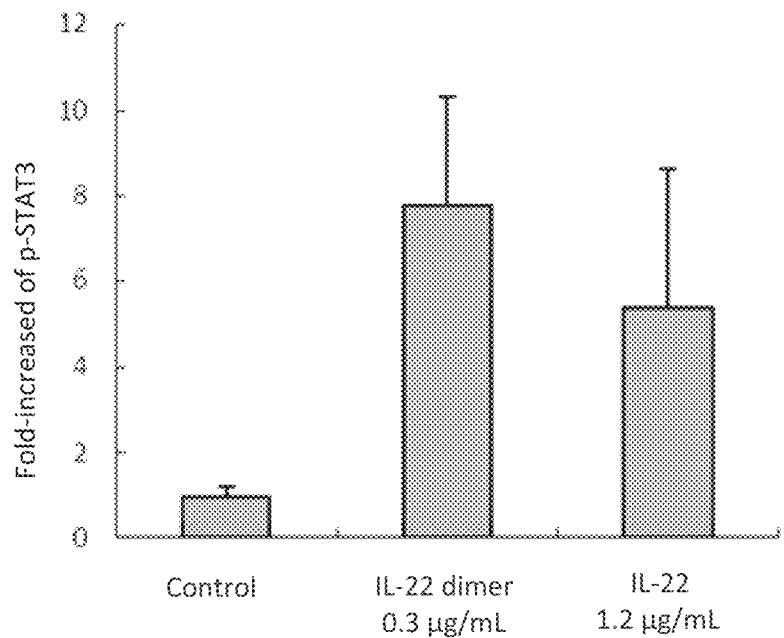

FIG. 4 shows the effect of IL-22 and IL-22 dimer (IL-22-Fc) on stimulating STAT3 in neurons. The result showed that both IL-22 and IL-22 dimer have the bioactivity of STAT3 activation in neurons, and the bioactivity of IL-22 dimer is significantly stronger than that of IL-22.

Figure 5:
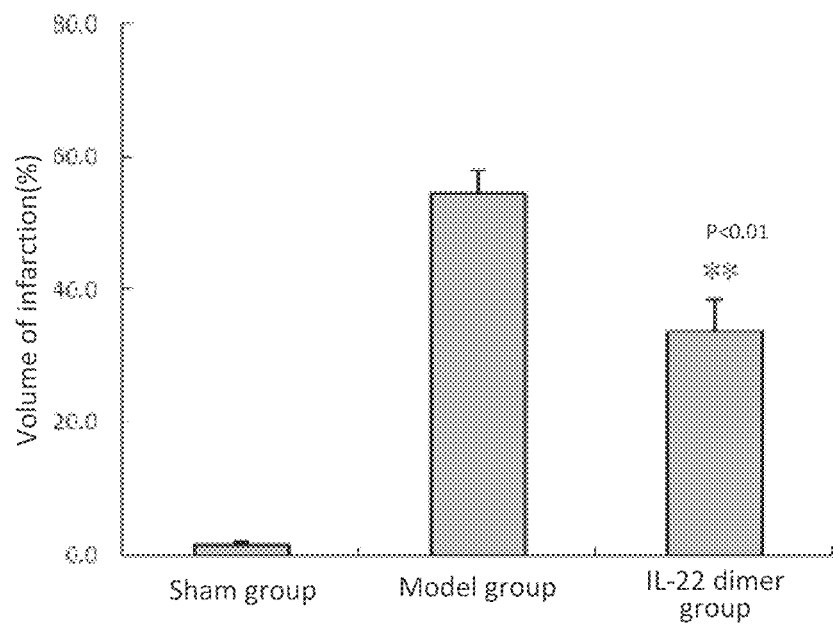

FIG. 5 shows the therapeutic effect of IL-22 dimer of the present invention on focal cerebral ischemia animal model. Recombinant human IL-22 dimer was shown to significantly decrease the volume of cerebral infarction.

Figure 6:
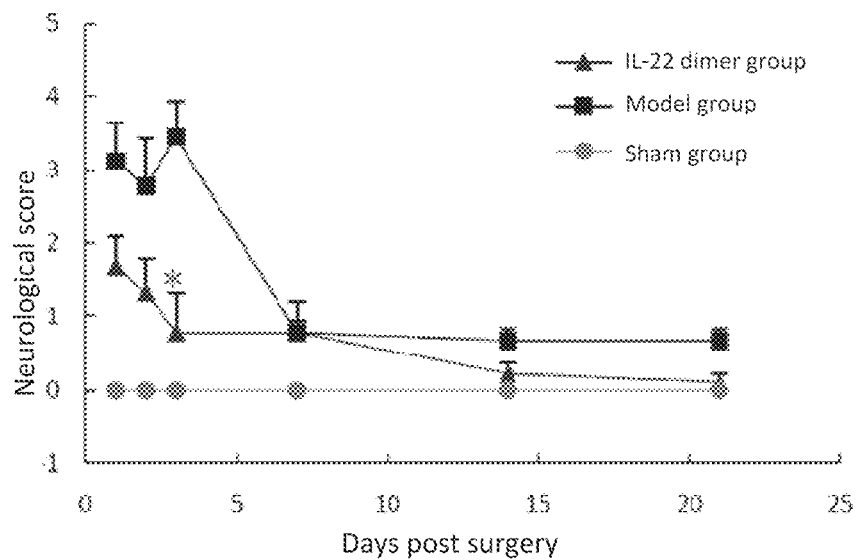

FIG. 6 shows the therapeutic effect of IL-22 dimer of the present invention on focal cerebral ischemia animal model. Recombinant human IL-22 dimer was shown to significantly improve the neurological function of the animal model.

Figure 7:
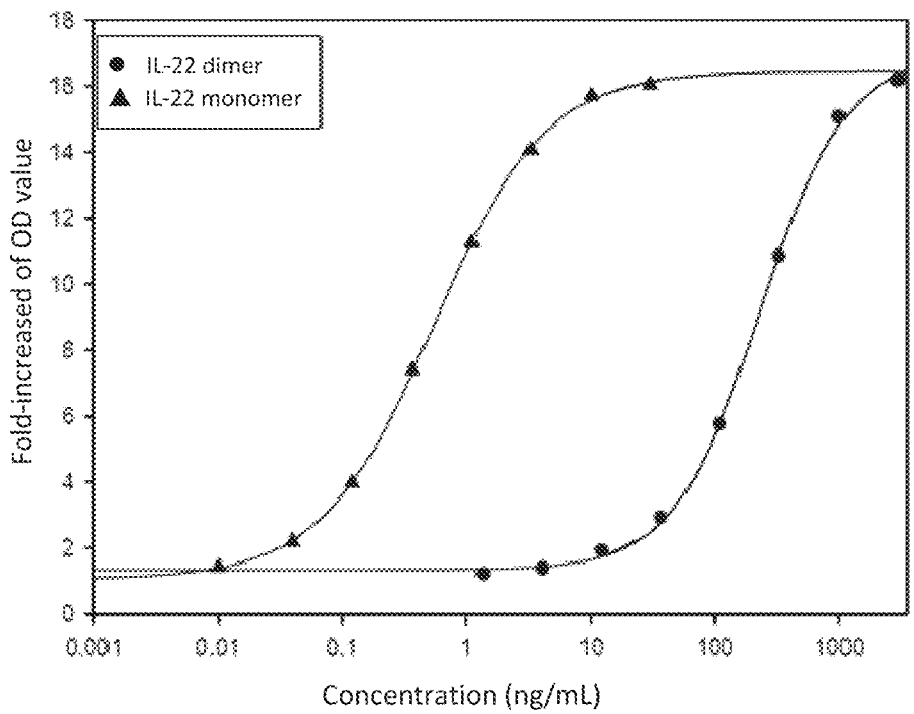

FIG. 7 shows the results of analysis on the in vitro bioactivity of IL-22 dimer and IL-22 monomer.

Figure 8A:
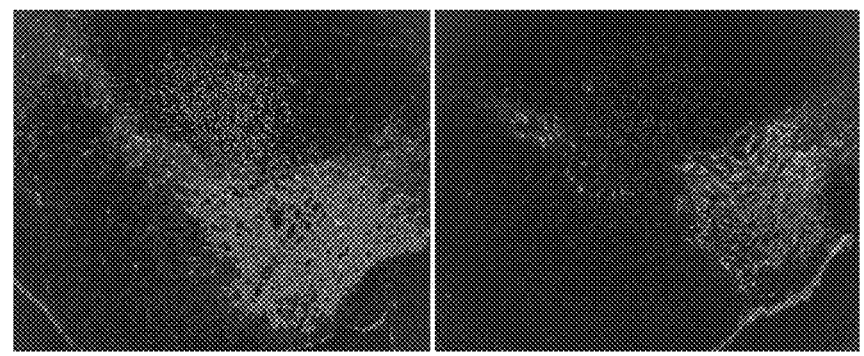
Figure 8A:
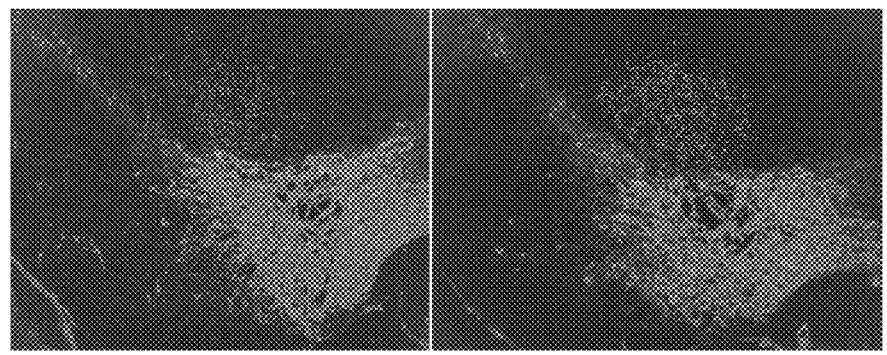

FIG. 8A is a series of representative graphs showing the immunohistochemical staining of TH-positive neurons in mouse substantia nigra pars compacta.

Figure 8B:
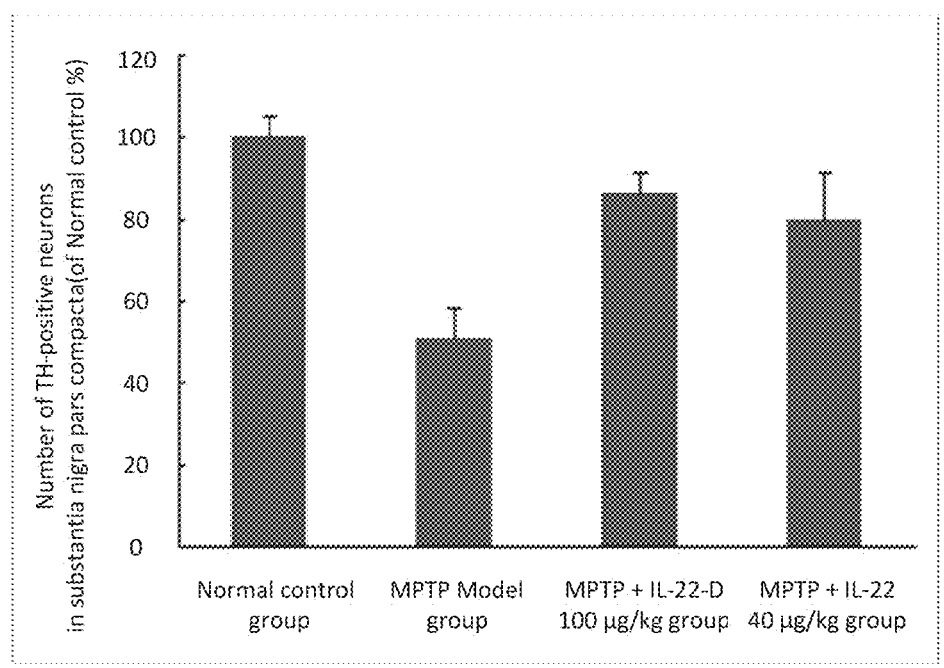

FIG. 8B shows the results of TH-positive cell counting in mouse substantia nigra pars compacta.

DETAILED DESCRIPTION OF THE PREFERRED EMBODIMENTS

Upon an extensive and thorough study, the inventors have, for the first time ever, surprisingly found that IL-22 or IL-22 dimer has a significant therapeutic effect in nerve damage diseases or neurodegenerative diseases. In addition, as compared to IL-22 monomer, the IL-22 dimer of the present invention has a prolonged in vivo half-life, can improve pharmacokinetic properties of the drug, reduce the injection frequency, and has significantly enhanced in vivo bioactivity. As shown in the experiment of activation of STAT3 in neurons, the IL-22 dimer can increase signal level of p-STAT3 in neurons more significantly than that of IL-22 monomer on molar basis concentration of IL-22 molecule, in which the final molar concentration of IL-22 dimer is one-tenth that of IL-22 monomer. Therefore, the IL-22 dimer has a better protective effect on neurons, enabling more effective treatment of nerve damage diseases. In addition, the IL-22 dimer can effectively prevent neuronal loss, thereby enabling more effective treatment of neurodegenerative diseases. This invention is achieved upon these surprising discoveries.

Terms

The term "essentially the same amino acid sequence" means that the amino acid sequence is identical; or that within the amino acid sequence, there is a change in one or more amino acid residues (missing, addition or replacement of one or more residues), and such change essentially would not decrease the biological activity thereof, i.e., the amino acid sequence can still exert its biological function upon binding to IL-22 receptors in target cells. Any such "essentially the same" IL-22, either glycosylated (derived from natural or eukaryotic expression system) or un-glycosylated (derived from prokaryotic expression system or chemically synthesized), is within the scope of the present invention.

The term "therapy" refers to administration of IL-22 to a subject in need thereof in order to cure, ameliorate, improve, reduce or affect the disease, symptom, or predisposition of the subject.

The term "subject" refers to mice, human and other mammals.

The term "therapeutically effective dose" refers to a dose of IL-22 which can achieve the goal of treatment within the subject in need thereof. It is to be understood by one of ordinary skills in the art that, "therapeutically effective dose" may vary depending on the routes of administration of IL-22, the types of excipients used and the combination with other medicaments.

IL-22 and the Preparation Thereof

As used herein, the term "Interleukin-22" or "IL-22" refers to a protein, which (a) has essentially the same amino acid sequence as the human/murine IL-22 as described by Dumoutier et al. in U.S. Pat. No. 359,117 and (b) the same biological activity as natural IL-22. IL-22 of the present invention includes but is not limited to human IL-22, recombinant human IL-22, murine IL-22 and/or recombinant murine IL-22. In the present invention, the term "IL-22" includes monomer, dimer or multimer forms of IL-22.

"IL-22" also includes pegylated IL-22 and covalently modified IL-22 proteins. For example, the IL-22 in the present invention can be polymerized by the modification with any activated polyethylene glycol (PEG) with molecular weight of 5,000-100,000 for the purpose of prolonging its half-life time. Detailed protocols can be referred to in Greenwald et al., Bioorg. Med. Chem. Lett. 1994, 4, 2465; Caliceti et al., IL Farmaco, 1993, 48,919; Zalipsky and Lee, Poly (Ethylene Glycol) Chemistry: Biotechnical and Biomedical Applications, J. M. Harris, Plenus Press, New York (1992). Multi-arm branched active PEG is preferred (CN ZL02101672.0, WO9932139, PCT/US95/0755, PCT/US94/13013, U.S. Pat. No. 4,640,835, U.S. Pat. No. 4,496,689, U.S. Pat. No. 4,301,144, U.S. Pat. No. 4,670,417, U.S. Pat. No. 4,791,192, U.S. Pat. No. 4,179,337).

IL-22 of the present invention can be expressed by gene recombination technology. The expressing host cell includes prokaryotic cell, yeast cell or higher eukaryotic cell. Suitable prokaryotic host cell includes but is not limited to $G^+$ or $G^-$ bacteria, such as *E. coli*. Publicly available *E. coli* strains include K12 MM294 (ATCC 31,446), X1776 (ATCC 31,537), W3110 (ATCC 27,325) and K5 772 (ATCC 53,635), etc. Other suitable prokaryotic cells include but are not limited to *Erwinia, Klebsiella, Proteus*, etc. *E. coli* W3110 is preferred since it is often used as the host cell for recombinant DNA product.

Apart from prokaryotic cells, eukaryotic cells such as filamentous fungi or yeast are also suitable for expression or cloning of IL-22 of the present invention. *Saccharomyces* is a common lower eukaryotic host microorganism. Other host cells include *Schizosaccharomyces pombe, Kluyveromyces* hosts, *PichiaPastoris*, etc. Methylotropic yeasts may also be used to express the IL-22 of the present invention, including but not limited to various types of yeast that can grow in methanol such as *Hansenula, Candida, Kloeckera, Pichia, Saccharomyces*, etc.

Host cells used to express glycosylated IL-22 of the present invention can be derived from multicellular organism. Examples of invertebrate cells include insect such as *Drosophila* S2 and *Spodoptera* Sf9, and plant cells. Suitable mammalian host cells include Chinese Hamster Ovary (CHO), COS cells; in particular, SV40-transformed monkey kidney CV1 cell line (COS-7, ATCC CRL 1651) and human embryo kidney cell line 293, etc. One of ordinary skills in the art should be aware of how to select the suitable host cells.

The above mentioned host cells can be grown on conventional nutrient media after transformation or transfection with IL-22 expression vector or cloning vector. The aforesaid nutrient media, upon modification, is suitable for inducing promoter, selecting transformant or amplifying IL-22 encoding sequence. The conditions for cultivation such as selection of nutrient media, temperature and pH are clear to one of ordinary skills in the art. For the general principles for optimizing the proliferation of cultured cells, protocols and techniques thereof, see Mammalian Cell Biotechnology: a Practical Approach, M. Butler, ed. (IRL Press, 1991) and Sambrook et al., supra.

The method of transfecting eukaryotic cells and transforming prokaryotic cells would be clear to one of ordinary skills in the art, such as method of using calcium chloride ($CaCl_2$), calcium phosphate precipitation, lipofectamine or electroporation. One skilled in the art would be able to select the suitable standard method depending on the different host cells used. For example, method using $CaCl_2$ (Sambrook et al., supra.) or electroporation is generally suitable for eukaryotic cells; calcium phosphate precipitation may be used for those mammalian cells without cell walls.

The nucleotide sequence (i.e., cDNA or genomic DNA) encoding IL-22 of the present invention can be inserted into a replicable vector for gene cloning (DNA amplification) or expression. All vectors, such as plasmid, cosmid, virion or bacteriophage are publicly available. With the use of common techniques in this field, one skilled in the art can insert the nucleotide sequence encoding IL-22 of the present invention into appropriate restriction endonuclease sites in a replicable vector following routine steps.

The IL-22 of the present invention can not only be directly expressed through gene recombination, but also be produced through fusion with heterologous polypeptides to form fusion polypeptides. The latter can be a signal sequence localized in the N-terminus of a mature protein or polypeptide, and can also be other polypeptide fragments with specific digestion sites localized in the N-terminus of a mature protein or polypeptide. Usually, the signal sequence is part of the above replicable vector, or part of the nucleotide sequence encoding IL-22 of the present invention inserted into a replicable vector.

Both the expression vector and the cloning vector have a piece of nucleotide sequence, which enables the vector to replicate in one or more corresponding host cells. The nucleotide sequences corresponding to the bacteria, yeast or virus host cells are known to one of ordinary skills in the art. For example, the origin of replication of plasmid pBR322 is suitable for most $G^-$ bacteria, the origin of replication of 2.mu. plasmid is suitable for yeast, while the origin of replication of viruses (SV40, polyoma virus, adenovirus, VSV or BPV) is suitable for cloning vector in mammalian cells.

Both the expression vector and the cloning vector usually have a piece of selecting gene, also referred to as "selecting marker". Typical protein encoded and expressed by selecting gene is (a) resistant to some antibiotics such as ampicillin, neomycin, methotrexate, tetracycline etc, or toxin; (b) able to remedy auxotrophic deficiencies; and (c) capable of supplementing some key nutrient factors, such as D-alanine racemase encoding sequence needed by *bacillus* hosts, that cannot be provided by complex media.

The selecting gene suitable for mammalian host cells should be able to distinguish the host cells that can accept IL-22 encoding gene of the present invention, such as DHFR or thymidine kinase. The suitable host cell using wild-type DHFR as the selecting gene is CHO strain without DHFR activity. The method of preparation and culture of this strain can be seen in Urlaub et al., Proc. Natl. Acad. Sci. USA, 77:4216 (1980). The selecting gene suitable for yeast cells is trp1 gene expressed in yeast plasmid Yrp7 (Stinchcomb et al., Nature, 282:39 (1979); Kingsman et al., Gene, 7:141 (1979); Tschemper et al., Gene, 10:157 (1980)). trp1 gene can be used to screen yeast mutant strains that cannot grow on tryptophan, such as ATCC No. 44047 or PEP4-1 (Jones, Genetics, 85:12 (1977)).

Both expression vector and clone vector usually include a promoter that can be manually ligated to the nucleotide sequence encoding IL-22 of the present invention, for directing mRNA synthesis. Promoters corresponding to all kinds of host cells are known to one skilled in the art. The promoters suitable for prokaryotic hosts include β-lactamase and lactose promoter system, etc. Bacterial host promoter also includes a piece of Shine-Dalgarno (S.D.) sequence that can be manually ligated to the nucleotide sequence encoding IL-22 of the present invention.

The transcription of the IL-22 encoding nucleotide sequence of the present invention in eukaryotic expression system can be enhanced through the insertion of enhancer into the replicable vectors. Enhancer is a type of cis-acting element of DNA molecule and is usually of the length of 10-300 bp, which can enhance the transcription of DNA molecules by acting on the promoters.

The expression vectors in eukaryotic host cells (yeast cells, fungi cells, insect cells, plant cells, animal cells, human cells, or other nucleated cells from other multicellular organisms) also include the nucleotide sequence for terminating transcription and stabilizing mRNA. This type of sequence is usually derived from the 5' terminal of untranslated region in eukaryotic cells, viral DNA or cDNA, and is sometimes derived from the 3' terminal. The nucleotide sequence within "the untranslated region" can be transcribed as acylated-polyA sequence at the untranslated region of mRNA of IL-22 of the present invention.

Other methods, vectors and host cells for synthesizing the IL-22 of the present invention in recombinant vertebrate culture system can be seen in Gething et al., Nature, 293:620-625 (1981); Mantei et al., Nature, 281:40-46 (1979); EP 117,060 and EP 117,058.

IL-22 Dimer

Figure 1:
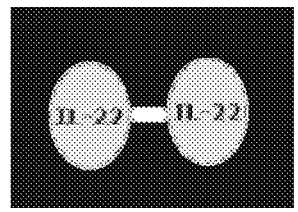
FIG. 1 is an illustration of an IL-22 dimer according to the present invention. In the figure, "-" represents a linker and the oval-shaped object labeled with "IL-22" represents an IL-22 monomer.

The structure of the IL-22 dimer of the present invention is shown as Formula I. FIGS. 1-3 illustrate the representative structures of the IL-22 dimer of the present invention, in which the carrier protein includes but is not limited to Fc fragment of human IgG (1, 2, 3, 4), or human albumin IL-22 can be localized at the C-terminal or N-terminal of the carrier protein.

As used herein, "linker" refers to a short peptide disposed between one IL-22 monomer and another IL-22 monomer and connecting the two monomers together. There is no special restriction on the length of the linker. A linker is usually 5-50 amino acid residues in length. In general, a linker does not affect or significantly affect the proper fold and conformation formed by the configuration of the two IL-22 monomers. Some examples of linkers include (but are not limited to):

Preferably, the linker contains an amino acid sequence selected from:
(a). an amino acid sequence with 3-16 hydrophobic amino acid residues Gly or Pro, such as Gly-Pro-Gly-Pro-Gly-Pro;
(b). an amino acid sequence encoded by multiple cloning sites. Such sequences usually contain 5-20 amino acid residues, preferably, 10-20 amino acid residues;
(c). an amino acid sequence of a protein other than IL-22 monomer, such as an amino acid sequence of IgG or albumin; and
(d). an amino acid sequence comprising any combination of (a), (b), and (c) above.

In one preferred embodiment, the linker has the sequence of GSGGGSGGGGSGGGGS (i.e. amino acid residues 147-162 of SEQ ID NO: 1) and ASTKGP (i.e. amino acid residues 147-152 of SEQ ID NO: 3).

In addition, an amino acid sequence not affecting the biological activity of IL-22 monomer can be added to the N-terminal or C-terminal of the fusion protein. In a preferred embodiment, such appended amino acid sequence is beneficial to expression (e.g. signal peptide), purification (e.g. 6×His sequence, the cleavage site of *Saccharomyces cerevisiae* α-factor signal peptide (Glu-Lys-Arg)), or enhancement of biological activity of the fusion protein.

Method of Dimer Preparation

DNA sequences encoding the IL-22 dimer or the fusion protein of the present invention can be entirely artificially synthesized. Alternatively, the DNA sequences encoding the first IL-22 monomer and/or the second IL-22 monomer can be obtained by PCR amplification or synthesis and then joined together to form the DNA sequence encoding the fusion protein of the present invention.

In order to enhance the expression volume of the host cells, modification can be performed on sequence encoding the IL-22 dimer. For example, codons preferred by the host cells can be used to eliminate sequences that are not beneficial to transcription and translation. In the present invention, codons preferred by yeast cells or mammalian cells can be used together with DNA software for assaying the gene of IL-22 dimer to eliminate sequences that are not beneficial to transcription and translation from the gene. The eliminated sequences can be intron cutting site, transcription terminating sequence, etc.

After the DNA sequence encoding the novel fusion protein of the present invention is obtained, it is first inserted into an appropriate expression carrier, followed by transformation into an appropriate host cell. Finally, the transformed host cells are cultivated and the novel fusion protein of the present invention is isolated and purified.

As used herein, the term "carrier" includes plasmid, cosmid, expression vector, cloning vector, and virus vector, etc.

In the present invention, carriers known in the art, such as carriers available in the market, can be used. For example, with the use of carrier obtained from the market, nucleotide sequence encoding the novel fusion protein of the present invention can be operationally connected to an expression control sequence to form the protein expression carrier.

As used herein, "operationally connected" refers to a scenario where some parts of a linear DNA sequence can affect the activity of other parts of the same linear DNA sequence. For instance, if signal peptide DNA is used for the expression of a precursor that participates in secretion of polypeptides, then said signal peptide (secretion leader sequence) DNA is "operationally connected" to the polypeptide DNA. If a promoter controls the transcription of a sequence, the promoter is "operationally connected" to the encoded sequence. If a ribosome binding site is situated at a position where translation thereof is made possible, said ribosome binding site is "operationally connected" to the encoded sequence. In general, "operationally connected" means that the residues of concern are in proximity; for secretion of the leader sequence, "operationally connected" refers to proximity within the reading frame.

As used herein, the term "host cells" refers to both prokaryotic cells and eukaryotic cells. Prokaryotic host cells commonly used include *E. coli, B. subtilis*, etc. Eukaryotic host cells commonly used include yeast cells, insect cells, and mammalian cells, etc. In a preferred embodiment, the host cells used are eukaryotic cells; in another preferred embodiment, the host cells used are mammalian cells.

After the transformed host cells are obtained, they can be cultivated under a condition suitable to express the fusion protein of the present invention for expressing the fusion protein. The expressed fusion protein is then separated.

Pharmaceutical Composition and Method of Administration Thereof

Since the IL-22 dimer of the present invention can generate a stronger receptor activation signal and has an excellent serum half-life, the IL-22 dimer of the present invention and a pharmaceutical composition comprising the IL-22 dimer of the present invention as the main active ingredient can be used for treatment and prevention of nerve damage diseases or neurodegenerative diseases. The said nerve damage diseases include: stroke, spinal injury, and neurological disorders accompanied with blood brain barrier injury. The neurodegenerative disease is selected from: Parkinson's disease, Alzheimer's disease, Huntington disease, amyotrophic lateral sclerosis, spinal muscular atrophy, primary lateral sclerosis, and spinal cerebellar ataxias.

The pharmaceutical composition of the present invention comprises a safe and effective amount of the IL-22 of the present invention or its dimer and a pharmaceutically acceptable excipient or carrier. "Safe and effective amount" refers to an amount of a compound sufficient to substantially improve the condition of the patient in need thereof, without causing serious side-effects. In general, the pharmaceutical composition comprises 0.001-1,000 mg of IL-22 or its dimer per dose; in a preferred embodiment, the pharmaceutical composition comprises 0.05-300 mg of IL-22 or its dimer per dose; in a more preferred embodiment, the pharmaceutical composition comprises 0.5-200 mg of IL-22 or its dimer per dose.

Composition of the present invention and its pharmaceutically acceptable salts can be made into various formulations, including a safe and effective amount of the IL-22 of the present invention or its dimer and pharmaceutically acceptable excipient or carrier. "Safe and effective amount" refers to an amount of a compound sufficient to substantially improve the condition of the patient in need thereof, without causing serious side-effects. The safety and effective amount of a compound are determined based on the age, condition, course of treatment of a subject of treatment and other specific factors.

"Pharmaceutically acceptable excipient or carrier" refers to one or more compatible solid or liquid filling or gelatin materials which are suitable to be used in human with sufficient purity and sufficiently low toxicity. "Compatibility" refers to the ability of each ingredient of the composition to mutually blend with the compound of the present invention and the mutual blending ability between the ingredients, without substantially decreasing the clinical efficacy of the compound. Some of the examples of pharmaceutically acceptable excipient or carrier include cellulose and its derivatives (e.g. sodium carboxymethylcellulose, sodium ethylcellulose, cellulose acetate, etc), gelatin, speckstone, solid lubricating agent (e.g. stearic acid, magnesium stearate), calcium sulphate, plant oil (e.g. pea oil, sesame oil, peanut oil, olive oil, etc.), polyols (e.g. propylene glycol, glycerol, mannitol, sorbitol, etc.), emulsifier (e.g. Tween®), wetting agent (e.g. sodium lauryl sulfate), colorant, flavoring agent, stabilizer, anti-oxidant, antiseptic, pyrogen-free water, etc.

Route of administration of the IL-22 or its dimer of the present invention comprises oral administration, rectal administration, parenteral administration (intravenous, intramuscular, or subcutaneous), and partial administration.

Solid form for oral administration comprises capsules, tablets, pills, powder, and granules. In these solid forms, active compound is mixed with at least one of the conventionally inert excipients (or carriers), such as sodium citrate, dicalciumphosphate, or any of the following ingredients: (a) filing or bulking agent, e.g. starch, lactose, sucrose, glucose, mannitol, and silicic acid; (b) adhesion agent, e.g. carboxymethylcellulose, alginate, gelatin, polyvinyl pyrrolidone, sucrose, and acacia; (c) humectants, e.g. glycerol; (d) disintegrating agent, e.g. agar, calcium carbonate, potato starch or cassava starch, alginic acid, certain compounded silicate, and sodium carbonate; (e) dissolution-retarding agent, e.g. paraffin wax; (f) absorption accelerating agent, e.g. quaternary amine compound; (g) wetting agent, e.g. cetanol and glycerin monostearate; (h) absorbent, e.g. bolus alba; and (i) lubricant, e.g. speckstone, calcium stearate, magnesium stearate, solid polyethylene glycol, sodium lauryl sulfate, or any mixture thereof. Capsules, tablets, and pills can also comprise buffering agent.

Solid form such as tablets, sugar pills, capsules, pills, and granules can be prepared with coating and core-shell materials, such as casing and other materials known in the art. These materials comprise opacifying agent and the active compound or compound in the composition can be released in a delayed fashion at a certain part of the alimentary canal. Embedding component such as polymer materials and wax materials can be used. If desired, active compounds can be mixed with one or more of the above-described excipients to formulate a micro capsule form.

Liquid forms for oral administration comprise pharmaceutically acceptable emulsion, solution, suspension, syrup, or tincture. Apart from active compounds, liquid forms also comprise inert diluents conventionally used in the art such as water or other solvent, solublilizing agent and emulsifier such as ethanol, isopropanol, carbonate acetate, ethyl acetate, propan-2-ol, 1,3-butan-2-ol, dimethylformamide, and oil; in particular cotton seed oil, peanut oil, maize embryo oil, olive oil, castor oil, and sesame oil, or any mixture thereof.

Apart from the inert diluents, the composition can also comprise additives, such as wetting agent, emulsifying agent, suspending agent, sweetening agent, correctives, and spices.

Apart from the active compounds, suspension can also comprise suspending agent, such as ethoxylisostearic alcohol, polyoxyethylene sorbitol, sorbitan, microcrystalline cellulose, aluminiummethoxide, agar, or any mixture thereof.

Compositions used for parenteral administration can also comprise physiologically acceptable sterile water or anhydrous solution, dispersion solution, suspension, or emulsion, and sterile powder that can be re-dissolved into sterile injectable solution or dispersion solution. Suitable hydrated or anhydrous carriers, diluting agent, solvent, or excipient comprise water, ethanol, polyols, and appropriate mixtures thereof.

Forms of the IL-22 or its dimer of the present invention used for partial administration comprise ointment, powder, patch, sprayer, and inhalant. Under sterile conditions, the active components can be mixed with physiologically acceptable carrier and any antiseptic, buffering agents, or propellant if desired.

The IL-22 or its dimer of the present invention can be solely administrated or be administrated in conjunction with any other pharmaceutically acceptable compounds.

The micro-capsule containing IL-22 or its dimer of the present invention can be used as a sustained release system. Sustained release micro-capsule system of recombinant protein has been successfully applied to recombinant human growth hormone (rhGH), recombinant human interferon (rhIFN), IL-2 and MNrgp120 (Johnson et al., Nat. Med., 2:795-799 (1996); Yasuda, Biomed. Ther 27:1221-1223 (1993); WO 97/03692, WO 96/40072, WO 96/07399; U.S. Pat. No. 5,654,010).

The sustained release system of IL-22 or its dimer of the present invention can be prepared with poly(lactic-co-glycolic acid) (PLGA) which has good biologically compatibility and broad biological degradability. Lactic acid and glycolic acid, the degrading products of PLGA, can be cleared quickly in human body. Furthermore, the degradability of that polymer can vary from several months to several years depending on its molecular weight and composition (Lewis, "Controlled release of bioactive agents form lactide/glycolide polymer," in: M. Chasin and R. Langer (Eds.), Biodegradable Polymers as Drug Delivery Systems (Marcel Dekker: New York, 1990), pp. 1-41)).

The dosage and concentration of the pharmaceutical composition of the present invention can be adjusted according to actual use situation. One skilled in the art should know how to choose the suitable dosage and route of administration according to practical needs. The principle for adjusting between different species such as mice and human can be seen in Mordenti, J. and Chappell, W. "The use of interspecies scaling in toxicokinetics" In Toxicokinetics and New Drug Development, Yacobi et al.; Pergamon Press, New York 1989, pp. 42-96.

When using the pharmaceutical composition, a safe and effective amount of the IL-22 or its dimer of the present invention is administrated to a mammal (e.g. human) in need thereof, in which the dosage administrated is a pharmaceutically acceptable effective administration dosage. For a human of 60 kg, the administration dosage is usually 0.01-300 mg, preferably 0.5-100 mg. In determination of the actual dosage, factors known in the art such as administration route, condition of the patients, etc. have to be considered, all of which are within the technical scope of doctors skilled in the art.

The main advantages of the present invention include:

1. IL-22 or its dimer can activate STAT3 in neurons in vitro.

2. IL-22 dimer has been proven to be effective in the treatment of nerve damage diseases in animal models.

3. IL-22 dimer can prolong in vivo half-life, improve pharmacokinetic properties of the drug thereof, reduce the injection frequency, and significantly enhance in vivo bioactivity.

4. IL-22 or IL-22 dimer can significantly inhibit the loss of dopaminergic neurons in substantia nigra and stimulate the function of dopaminergic neuron in animal model of PD.

5. IL-22 or IL-22 dimer can significantly reduce the apoptosis of neurons in hippocampus and improve learning and memory capacity of AD animal model.

6. IL-22 or IL-22 dimer has a remarkable neuro-protective effect in neurodegenerative diseases, enabling therapeutic efficacy in the treatment of neurodegenerative diseases.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein. Further, for the embodiments in which details of the experimental methods are not described, such methods are carried out according to conventional conditions such as those described in Sambrook et al. Molecular Cloning: A Laboratory Manual (New York: Cold Spring Harbor Laboratory Pres, 1989), or suggested by the manufacturers.

Example 1

The IL-22 dimer with the structure described in FIGS. 1-3 having an amino acid sequence of SEQ ID NO: 1 or comprising monomers with amino acid sequences as shown in SEQ ID NOs: 2-5, is prepared and purified by conventional methods. For example, the IL-22 dimer comprising IL-22-Fc complexes was prepared. Preparation methods are described as follows:

a. Construction of a Cell Line Expressing IL-22 Dimer

The cDNA sequences encoding IL-22-Fc complexes (as shown in SEQ ID NO: 6 or SEQ ID NO: 7, wherein SEQ ID NO: 6 encodes the monomer shown in SEQ ID NO: 2, and SEQ ID NO: 7 encodes the monomer shown in SEQ ID NO: 3) were synthesized. The cDNA sequence of human IL-22 monomer was connected with the cDNA sequence of Fc fragment of IgG2. EcoRI site and components required for mammalian cell expression such as Kozak sequence and signal peptide sequence were introduced at the 5' end, while XbaI site was introduced at the 3' end. It was cloned into a commercially available pUC19 plasmid, which was then named as pIL-22-Fc and transformed into E. coli TG1. pUC19 plasmid was digested with EcoRI and XbaI, and an approximately 1300 bp of IL-22-Fc fragment was harvested and connected with EcoRI and XbaI digested expression plasmid pcDNA3 (Invitrogen) to construct expression plasmid pEX-IL-22-Fc. Expression plasmid pEX-IL-22-Fc was linearized and transfected into CHO cells to express IL-22 dimer. The expression level was measured by ELISA method and cell lines with a higher protein yield were screened and cell banks were prepared.

b. Separation and Purification of IL-22 Dimer

Recombinant CHO cells were cultured by conventional method to express recombinant protein. After cell culture, the cell supernatant was harvested (containing IL-22 complexes, IL-22 dimers, IL-22 multimers and metabolites). The collected supernatant was filtered and purified by a series of chromatography methods. For example, it was captured by a rProtein A Sepharose FF (GE Healthcare, Cat: 17-1279-04), eluted with a buffer containing 20-50 mM citrate acid and 0.1-2 M NaCl at pH 3.5-3.8, to obtain IL-22 dimer of purity greater than 90%, then the next step was performed by using mixed-mode PPA chromatography (PALL Life Sciences Cat: k364-01) and the target protein was eluted with a buffer solution of 20-50 mM NaAc/HAC at pH 3.0-5.0. The eluate was subject to low pH inactivation and Nano 20 membrane filtration for viral removal. The IL-22 dimer was ultimately obtained.

The purity of the isolated and purified IL-22 dimer was greater than 95% (using reverse phase HPLC analysis). As illustrated by electrophoresis, the molecular weight of the purified IL-22 dimer (consisting of two monomers shown in SEQ ID NO: 2) was 52±10 KD (using reduced SDS-PAGE analysis) which matched the predicted value. The maximum UV absorption wavelength was 280 nm. IL-22 dimers can stimulate Colo205 cells to produce IL-10 in vitro (The ED50 was 10-1000 ng/mL).

Example 2

In Vivo Half-Life of IL-22 Dimer

Rats received a single subcutaneous injection of IL-22 dimer (consisting of two IL-22-Fc monomers comprising a sequence shown in SEQ ID NO: 2) with a dosage of 100 µg/kg. The pharmacokinetic parameters were calculated and listed in Table 1 below (n=6). The in vivo half-life of IL-22 monomer (recombinant human IL-22) in rats was approximately 1.3 hr.

TABLE 1

| Parameter (n = 6) | Unit | Average Value | SD |
|---|---|---|---|
| $AUC_{(0-t)}$ | ng/mL * h | 4216.7 | 638.3 |
| $MRT_{(0-t)}$ | h | 22.6 | 1.6 |
| $t_{(1/2)}$ | h | 7.8 | 1.3 |
| Clz/F | L/h/kg | 0.028 | 0.003 |
| $C_{max}$ | ng/mL | 153.2 | 26.2 |

Example 3

Effect of IL-22 or IL-22 Dimer on STAT3 Activation in Neurons

Fetal rat brain was harvested from female SD rats at the 17$^{th}$ day of gestation, and then placed in pre-chilled D-Hanks solution. Cerebral cortex without meninx was carefully removed under dissection microscope and cut into small pieces of approximately 1 mm$^3$. The minced cortex was digested in 10 mL of 0.125% of trypsin, at 37° C. for 15 min. Then the tissue was aspirated and transferred into pre-chilled centrifuge tubes containing DMEM containing 10% FBS, and pipetted for a few times with a pipettor to stop the trypsin digestion. After standing, the supernatant was obtained and aspirated into another centrifuge tube. Such steps were repeated for 2-3 times.

The cells were cultured in serum-free neuron basal medium (Invitrogen, Cat: 21103049) with serum-free additive of B27 (Invitrogen, Cat: 17504044) for 8 days. The medium was replaced once every two days.

After 8 days of culture, the neurons were treated with various concentrations of IL-22 dimer (consisting of two IL-22-Fc monomers comprising a sequence shown in SEQ ID NO: 2) or IL-22 for 15 min (the final concentration of IL-22 dimer was 0.3 µg/mL, and the final concentration of IL-22 was 1.2 µg/mL), respectively. After completely removing the medium containing the drugs, the cells were washed twice with PBS and lysed with cell lysis buffer (Cell Signaling Technology, Cat: 9803; main ingredients containing 20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM $Na_3VO_4$, 1 µg/mL leupeptin, and 1 mM PMSF) according to the instruction thereof. The cells were lysed on ice for 20 min and scratched using cell scraper. Cell lysate was harvested and centrifuged at 12,000 rpm, 4° C. for 10 min.

The supernatant was collected and protein concentration was determined. Additionally, the change in STAT3 phosphorylation level was measured in 100 μL of the supernatant using a STAT3 [pY705] ELISA kit (Invitrogen, Cat: KH00481).

As shown in FIG. 4, in comparison to the control group, both IL-22 and IL-22 dimer can activate signal transduction and the biological activity of transcription factor 3 (STAT3) in neurons. IL-22 monomer (at a final concentration of 1.2 μg/mL) can increase the signal level of p-STAT3 in neurons to 5.4 times, whereas IL-22 dimer (at a final concentration of 0.3 μg/mL, which is at one-tenth of that of IL-22 monomer) can increase the signal level of p-STAT3 in neurons to 7.8 times. The results showed that the effect of IL-22 dimer on the activation of STAT3 in neurons is significantly stronger than that of IL-22 monomer.

Example 4

Therapeutic Effect of IL-22 Dimer in Focal Cerebral Ischemia Animal Model

Male SD rats, weighing 250-300 g were divided into 3 groups: a model group (received MCAO+ solvent, n=12), an IL-22 dimer group (received MCAO+ IL-22-D 100 μg/kg, IL-22-D consisting of two IL-22-Fc monomers comprising a sequence of SEQ ID NO: 2), and a sham group (received surgery+solvent, n=12).

Under anesthesia, the right common carotid artery (CCA), right internal carotid artery (ICA) and right external carotid artery (ECA) were exposed by neck surgery. A thread occluder, encapsulated with silica gel at the tip, was inserted into the common carotid artery through the external carotid artery and then advanced into the internal carotid artery for a approximately 18.5±0.5 mm for occluding. Mild resistance indicated that the thread occlude was lodged in the middle cerebral artery and able to block blood supply to the middle artery. After 60 min of occlusion, reperfusion was allowed by withdrawing the thread occluder by approximately 10 mm. Rats in IL-22 dimer group were administered subcutaneously at a dose of 100 μg/kg at 0.5 hr and 48 hr after the reperfusion, respectively. Rats in the sham group and model group were administered subcutaneously with equal volume of solvent. Body temperature was kept at 36.5° C. during the entire surgery. Rats in the sham group only had the neck skin incised and the internal carotid artery dissected, without insertion of the thread occluder. The animals were euthanized and the brains were harvested on Day 21.

The brain tissues were sliced into 6 slices by a 2 mm coronal section mold. The slices were incubated for 20-30 min in a 2% solution of TTC solution at 37° C. away from light, and then fixed with 10% buffered formalin solution. The fixed slices were then photographed with a digital camera. The unstained areas with white color represent infracted volume. The infarct volume was expressed as a percentage and calculated using the formula: infarct volume %=(the area of the contralateral hemisphere—the non-infarct area of the homolateral hemisphere)/the area of the contralateral hemisphere*100%. The volume of infarct area was measured by the software Photoshop 7.0.

Clinical Assessment of Neurological Syndromes

The neurological function test was performed on the 0, 1, 2, 3 day or 0, 1, 2, 3, 7, 14, 21 day after the surgery. The grading scale of 0-5 was: 0—no neurologic functional deficit, 1—failure to extend left forepaw fully, 2—discontinuously circling to the left, 3—continuous circling to the left, 4—falling to the left, 5—depressed level of consciousness, failure to walk spontaneously.

As shown in FIGS. 5-6, the volume of infarct area of rats in model group was 54.7%. In comparison to the model group, injection of IL-22 dimer showed a significant therapeutic effect ($p<0.01$). The volume of infarct area of rats in IL-22 dimer group was 33.8%, which was reduced by 20.9% relative to that of model group. On day 3 of the surgery, the neurological score of IL-22 dimer group showed a significant difference ($p<0.05$) as compared to that of model group, indicating that IL-22 dimer can prevent necrosis of neurons and promote the recovery of neural function.

Example 5

Pharmacokinetics of IL-22 Dimer in Cynomolgus Monkey 8 adult healthy rhesus monkeys in which half of them were male with weight of 3-5 kg were randomly divided into 2 groups according to the weight of the animal. The groups were treated with IL-22 dimer at a dose of 30 or 100 μg/kg, in which each treatment group had 4 animals, half of them were male. Each group received subcutaneous injection of the corresponding dose of IL-22 dimer (consisting of two IL-22-Fc monomers shown in SEQ ID NO: 2) at the administration volume of 0.2 mL/kg body weight in single administration. 0.6 mL blood was collected at the saphenous veins of the lower extremity prior to the administration and at the half, $1^{st}$, $2^{nd}$, $4^{th}$, $8^{th}$, $16^{th}$, $24^{th}$, $48^{th}$, $72^{nd}$, $96^{th}$, $120^{th}$, $144^{th}$, $168^{th}$ hour after administration. Upon standing at room temperature for 30 min, the serum was separated and the concentration of IL-22 dimer in the serum was measured using an ELISA kit (Biolegend, Cat: 434507). Pharmacokinetic parameters were analyzed using a non-compartmental model on the detected results, and the results were shown in Table 2. In vivo half-life ($t\frac{1}{2}z$) of IL-22 in Cynomolgus monkey is about 2 hr.

TABLE 2

| | Pharmacokinetic Parameters (average value ± SD, n = 4) | | | | | |
|---|---|---|---|---|---|---|
| dose | AUC(0-t) mg/L*hr | MRT(0-t) hr | t½z hr | Tmax hr | CLz/F mL/h/kg | Cmax ng/mL |
| 30 μg/kg | 11.92 ± 0.91 | 50.5 ± 5 | 63.3 ± 38.9 | 17 ± 9.5 | 2 ± 1 | 172.3 ± 17.1 |
| 100 μg/kg | 39.9 ± 6.2 | 51.1 ± 4.7 | 65.6 ± 10.9 | 24 ± 0 | 2 ± 0 | 506.9 ± 115.7 |

Example 6

In Vitro Bioactivity Analysis of IL-22 Dimer and IL-22

Upon the stimulation of IL-22, some cells can produce IL-10. As a result, the bioactivity of IL-22 can be measured by testing the corresponding OD value. The methods are described as follows:

Colo205 cells (ATCC No. CCL-222, human colon cancer cell) were cultured in RPMI1640 10% FBS medium and the cells were grown to the logarithmic phase. Supernatant was discarded and PBS was added to wash away residual culture medium, followed by addition of 2-5 mL 0.25% Trypsin-EDTA for digestion. Then medium was added and mixed to uniformity by pipetting. Mixture was centrifuged at 1500 rpm for 5 min and cells were collected and prepared into $5.0*10^5$ Cell/ml cell suspension with basic medium. The suspension was added into the wells of 96-well plate (100 μL/well) and stayed overnight at 37° C., in 5% $CO_2$ incubator. On the next day, the 96-well plate was removed from the $CO_2$ incubator and centrifuged at 800 rpm for 5 minutes at 4° C. Then, 90 μL_of cell supernatant was withdrawn from each well and 90 μL 0.1% BSA/RPMI1640 was added to each well, followed by addition of IL-22 dimer (consisting of two monomers comprising a sequence shown in SEQ ID NO: 2) to the final concentration of 1.4, 4.1, 12.3, 37.0, 111.1, 333.3, 1000, 3000 ng/mL, IL-22 to the final concentration of 0.01, 0.04, 0.12, 0.37, 1.1, 3.3, 10, 30 ng/mL. The mixture was incubated for 20 hours at 37° C. in 5% $CO_2$ incubator and cell supernatant was collected and the OD value thereof was tested using IL-22 ELISA kit (R&D, Cat: S1000B).

As shown in FIG. 7, the half effective concentration (ED50) value of IL-22 dimer is 229 ng/mL (2675 pM) and that of IL-22 is 0.54 ng/mL (32.4 pM).

As shown in the results above, although in vitro bioactivity of IL-22 is slightly better than that of the IL-22 dimer, in vivo pharmacokinetic parameters and effective activity of IL-22 dimer are far better than those of IL-22. It indicated that the bioactivity of IL-22 dimer should be assessed using in vivo experimental model.

The results of example 3 and 6 indicated that the effects of IL-22 monomer or dimer on various cells were quite different. For neural cells, the IL-22 dimer has a significantly stronger activation than IL-22 monomer. For human colon cancer cells (e.g. Colo205 cells), the IL-22 monomer has a slightly better activity than the IL-22 dimer.

Hence, the in vitro assay method of example 3 is more suitable for measurement of the biological activity of IL-22 dimer, especially the protective effect on neurons, and reflecting the bioactivity of IL-22 dimer in vivo.

Example 7

Protective Effect of IL-22 or IL-22 Dimer on PC12 Cells from $MPP^+$ Induced Neurotoxicity PC12 cell is a cell line derived from a pheochromocytoma of rats. The ability of PC12 in synthesis, metabolism, and delivery of dopamine has been shown in culture in vitro. PC12 cell line can be used as an in vitro model for screening active compounds.

PC12 cells were experimentally seeded at a density of 40,000 per well in 96-well plates in the following medium: DMEM, 10% horse serum +5% FCS, 1% Penicillin-Streptomycin. $MPP^+$ (Sigma) was added to final concentrations of 30-3000 μm. IL-22 was added to yield final concentrations of 0.04 ng/mL, 0.4 ng/mL, 4 ng/mL, and 40 ng/mL, respectively. IL-22 dimer (consisting of two IL-22-Fc monomers comprising a sequence selected from SEQ ID NOs: 2-5) was added at final concentrations of 0.1 ng/mL, 1 ng/mL, 10 ng/mL, and 100 ng/mL respectively. After 24 hr of incubation, cell viability was determined by a fluorimetric cell viability assay.

The results showed that the survival rate of PC12 cells decreases with increasing $MPP^+$ concentrations upon $MPP^+$ treatment, and that both IL-22 and IL-22 dimer show significantly protective effect on PC12 cells.

Example 8

Therapeutic Effect of IL-22 or IL-22 Dimer on an Animal Model of MPTP-Induced PD 1-methyl-4-phenyl-1,2,3,6-tetrahydropyridine(MPTP) can induce the massive loss of the dopaminergic neurons in substantia nigra by specifically injuring dopaminergic neurons, thereby resulting in syndromes similar to Parkinson's disease.

Male C57/BL6J mice of 12-14 weeks old, weighing ~28 g were used in this study. The animals were raised at a 24±2° C. room temperature, and kept under a 12 hr light/dark cycle with free access to food and water.

50 mice were randomly assigned to 5 groups with 10 mice in each group respectively: a solvent control group; a MPTP model group; a MPTP+IL-22 40 μg/kg group; a MPTP+IL-22-D 40 μg/kg group; a MPTP+IL-22-D 100 μg/kg group. The IL-22-D consisted of two IL-22-Fc monomers comprising a sequence selected from SEQ ID NOs: 2-5.

The mice were administrated via intraperitoneal injection of MPTP (30 mg/kg) for 5 consecutive days. After one day of recovery (i.e., from day 7), mice in the MPTP+IL-22 (40 μg/kg) group were daily administrated with IL-22 s.c. at a dose of 40 μg/kg for 7 consecutive days (i.e. from day 7 to day 13); mice in MPTP+IL-22-D 40 μg/kg group received IL-22-D s.c. at a dose of 40 μg/kg once on day 7, day 9 and day 11, respectively; mice in MPTP+IL-22-D 100 μg/kg group received IL-22-D s.c. at a dose of 100 μg/kg once on day 7, day 9 and day 11, respectively; mice in solvent control group received equal volume of saline s.c.

The animals were evaluated on the $14^{th}$ day as follows:

a. Behavioral Tests on Mice of PD

The behavior performance was tested on the $10^{th}$ day following the last administration of MPTP. The method was pole test which has been used to assess slow movement of the animals, a typical behavior in PD. (Matsuura et al., 1997; Araki et al., 2001; Kato et al., 2004)

Mice were carefully placed on the top of a rough pole (8 mm in diameter and 55 cm in height) with their heads facing upwards. The time required for a mouse to turn head from upwards to downwards completely was recorded as T-turn (time to turn). The time for a mouse to climb to the bottom of pole until their four legs arrive the ground was recorded as T-LA (locomotion activity time). Time exceeding 30 sec was recorded as 30 sec. The test was repeated 5 times and its average value was used for each mouse.

The results show that both IL-22 and IL-22 dimer can significantly improve the behavior performance in MPTP-induced mice.

b. Determination of the Concentration of Dopamine in Corpus Striatum

Methods: After mice were sacrificed by decapitation, the striatum tissues were removed and kept in 1.5 mL centrifuge tube after weighing, then immediately put in ice. 300 μL sample processing solution (0.02 M perchloric acid, 0.2 mM sodium pyrosulfite, 0.01% EDTA-2Na, containing 0.3 μM DHBA as an internal standard) was added to each 10 mg of sample in ice water bath. The above mixtures were homogenized by ultrasonic apparatus and then centrifuged at 10,000 g for 20 min at 4° C. The supernatants were removed and filtered through a 0.22 μM filter membrane. The concentrations of striatal dopamine were quantified using high performance liquid chromatography.

The results show that both IL-22 and IL-22 dimer can significantly inhibit the decrease of the concentration of striatal dopamine in MPTP-induced mice.

c. Observation of Dopaminergic Neurons in Substantia Nigra

Methods: Mice were anesthetized with 10% chloral hydrate. After perfusion with 4% paraformaldehyde, brains were removed and fixed with 4% paraformaldehyde for 24 hours. The samples were transferred in 10%, 20%, 30% sucrose solutions gradient dehydration until sinking to the bottom. The midbrains and striatums were coronally sectioned into slices with thickness of 15 μm at −20° C. by freezing microtome. TH is a specific marker for dopaminergic neurons. The slices of striatum and midbrain were incubated with the primary antibody which was a mouse monoclonal anti-TH antibody (1:1,000, CHEMICON) overnight at 4° C. After rinses in PBS for three times, the slices were incubated with biotin-conjugated secondary antibody at room temperature for 1 hr. SABC complexes were incubated at room temperature for 1 hr, followed by DAB staining, gradient dehydration in ethanol, transparency in xylene and the slides were sealed with neutral balsam. The optical density of TH-positive staining in the striatums was scanned and the number of TH-positive cells in the substantia nigra was counted.

The results showed that both IL-22 and IL-22 dimer significantly protected from the massive loss of dopaminergic neurons induced by MPTP.

Example 9

Effect of IL-22 or IL-22 Dimer on STAT3 Activation in Hippocampal Neuron

Fetal rat brain was harvested from female SD rats at the 17$^{th}$ day of gestation, and then placed in pre-chilled D-Hanks solution. Hippocampus was removed under dissection microscope and cut into small pieces of approximately 1 mm$^3$. The minced hippocampus was digested in 10 mL of 0.125% of trypsin, at 37° C. for 15 min. Then the tissue was aspirated and transferred into pre-chilled centrifuge tubes containing DMEM containing 10% FBS, and pipetted for a few times using a pipettor to stop the trypsin digestion. After standing, the resulting supernatant was transferred to another centrifuge tube. Such steps were repeated for 2-3 times.

The cells were cultured in serum-free neuron basal medium (Invitrogen, Cat: 21103049) with serum-free additive of B27 (Invitrogen, Cat: 17504044) for 8 days. The media was replaced once every two days.

After 8 days of culture, the neurons were treated respectively with various concentrations of IL-22 dimer (consisting of two IL-22-Fc monomers comprising a sequence selected from SEQ ID NOs: 2-5) (the final concentrations of IL-22 dimer were 1, 10, 100 ng/mL) or IL-22 (the final concentrations of IL-22 were 0.4, 4, 40 ng/mL) for 15 min, respectively. After completely removing the medium, the cells were washed twice with PBS and lysed with cell lysis buffer (Cell Signaling Technology, Cat: 9803, containing 20 mM Tris-HCl (pH 7.5), 150 mM NaCl, 1 mM Na$_2$EDTA, 1 mM EGTA, 1% Triton, 2.5 mM sodium pyrophosphate, 1 mM beta-glycerophosphate, 1 mM Na$_3$VO$_4$, 1 μg/mL leupeptin, and 1 mM PMSF as main ingredients) according to the instruction thereof. The cells were lysed on ice for 20 min and scratched using cell scraper. Cell lysate was harvested and centrifuged at 12,000 rpm, 4° C. for 10 min. The supernatant was collected and protein concentration was determined. Additionally, the change in STAT3 phosphorylation level was measured in 100 μl_of the supernatant using a STAT3 [pY705] ELISA kit (Invitrogen, Cat: KH00481).

The results show that both IL-22 dimer (IL-22-D) and IL-22 monomer can activate the biological activity of STAT3 in hippocampal neuron.

Example 10

Protective Effect of IL-22 or IL-22 Dimer on Aβ-Induced Apoptosis of PC12 Cells

The neurite outgrowth of PC12 cells induced by the nerve growth factor(NGF) indicates that PC12 cells have characteristics of neurons. Amyloid β(Aβ)-induced apoptosis of PC12 cell line can be used as an in vitro AD model.

PC12 cells were cultured in basic culture medium (DMEM, 10% FCS, 1% Penicillin-Streptomycin), digested with trypsin, and resuspended in medium containing 50 ng/mL of NGF. PC12 cells were seeded at a density of $2 \times 10^4$ per well in 96-well plates and incubated at 37° C., 5% CO$_2$ in an incubator for 24 hr. Aβ was added to yield final concentrations of 1-100 mmol/L. The cells were incubated with IL-22 monomer at final concentrations of 0.4, 4, 40 ng/mL respectively, or IL-22-D (consisting of two IL-22-Fc monomers comprising a sequence selected from SEQ ID NOs: 2-5) at final concentrations of 1, 10, 100 ng/mL respectively. Equal volume of PBS was added to the model wells and no Aβ was added to the negative control wells. After incubation for another 24 hr, cell morphology was determined by Hochest staining and PC12 cell proliferation was determined by MTT assay.

Compared to the negative control wells, the result of fluorescent nuclear staining of PC12 cells in the model wells was found to be obviously heterogeneous, showing solid and thick staining of hyperfluorescence of nucleus resulting from cell apoptosis, and that of IL-22 monomer treated cells or IL-22 dimer treated cells was found to be well-distributed without solid and thick staining of hyperfluorescence of nucleus. Both IL-22 and IL-22 dimer were able to inhibit the apoptosis of PC12 cells induced by Aβ upon differentiation stimulated by NGF and protect the nerve cells.

Example 11

Therapeutic Effect of IL-22 or IL-22 Dimer on MPTP-Induced Animal Model of PD 1-methyl-4-phenyl-1,2,3,6-tetrahydropyridine(MPTP) can induce the massive loss of the dopaminergic neurons in substantia nigra by specifically injuring dopaminergic neurons, resulting in syndromes similar to Parkinson's disease. Tyrosin hydroxylase (TH) which is a specific marker for dopaminergic neurons, can be used to quantitatively detect the number of dopaminergic neurons in substantia nigra.

The ratio of molecular weight of IL-22 monomer and IL-22-D is approximately 1:5, and one IL-22-D contains two IL-22 monomers. In order to compare the results, the equal molar dosage (calculated as IL-22 monomer) was used in this study, namely, the dosage of IL-22 was 40 μg/kg, while the dosage of IL-22-D was 100 μg/kg.

Male C57/BL6J mice of 12-14 weeks old, weighing 22-30 g were randomly divided into 4 groups:

MPTP+IL-22 40 µg/kg group: The animals received daily injection of MPTP at 30 mg/kg intraperitoneally for 5 consecutive days and allowed one day for recovery (from day 7) followed by subcutaneous administration of IL-22 (recombinant human IL-22) at a dose of 40 µg/kg for 7 consecutive days.

MPTP+IL-22-D 100 µg/kg group: The animals received daily injection of MPTP at 30 mg/kg intraperitoneally for 5 consecutive days and allowed one day for recovery (from day 7) followed by subcutaneous administration of IL-22-D at a dose of 100 µg/kg once on Day 7, 9, 11 respectively.

MPTP model group: The animals received daily injection of MPTP at 30 mg/kg intraperitoneally for 5 consecutive days and allowed one day for recovery followed by administration of equal volume of solvent (0.5% rat serum/PBS) from Day 7.

Normal control group: The animals received daily injection of equal volume of saline for 5 consecutive days and allowed one day for recovery followed by administration of equal volume of solvent (0.5% rat serum/PBS) from Day 7.

The aforesaid IL-22 dimer (IL-22-D) consisted of two IL-22-Fc comprising a sequence shown in SEQ ID NO: 2. Also, IL-22-D can consist of two IL-22-Fc monomers comprising a sequence selected from SEQ ID NOs: 3-5.

The animals were sacrificed on Day 14. The assessment of the condition of dopaminergic neurons in substantia nigra was performed.

Observation of Dopaminergic Neurons in Substantia Nigra

Methods: Mice were anesthetized with 10% chloral hydrate. After perfusion with 4% paraformaldehyde, brains were removed and fixed with 4% paraformaldehyde for 24 hours. The samples were transferred into 10%, 20%, 30% sucrose solutions gradient dehydration until sinking to the bottom. The midbrains were coronally sectioned into slices with thickness of 20 µm at −20° C. by freezing microtome, followed by TH immunohistochemical staining analysis. The slices of midbrain were incubated with the primary antibody which was a mouse monoclonal anti-TH antibody (1:1,000, Sigma) overnight at 4° C. After rinses in PBS for three times, the slices were incubated with biotin-conjugated secondary antibody (goat anti-mouse) at room temperature for 1 hr. SABC complexes were incubated at room temperature for 1 hr, followed by DAB staining, gradient dehydration in ethanol, transparency in xylene and the slides were sealed with neutral balsam. The number of TH-positive cells in substantia nigra pars compacta was counted.

The results were shown in FIG. 8A and FIG. 8B.

FIG. 8A shows the immunohistochemical staining of TH-positive neurons in substantia nigra pars compacta in mice. The TH-positive neurons dropped greatly in substantia nigra pars compacta after the mice received 5 consecutive days injection of MPTP. IL-22 or IL-22 dimer treatment significantly restored the number of TH-positive neurons.

FIG. 8B shows the results of the number of TH-positive cells in substantia nigra pars compacta in mice. Compared to normal control group, the number of TH-positive neurons (about 51% of the normal control) was significantly reduced in substantia nigra pars compacta in MPTP model group, indicating that MPTP induced massive loss of dopaminergic neurons in substantia nigra. The number of TH-positive dopaminergic neurons in substantia nigra of MPTP+IL-22 40 µg/kg group was about 80% of normal control group, and that of MPTP+IL-22-D 100 µg/kg group was about 86% of normal control group.

The results demonstrated that IL-22 or IL-22 dimer can protect dopaminergic neurons from the massive loss induced by MPTP (the protection of IL-22 dimer is more significant), thus has a therapeutic effect on degenerative change of dopaminergic neurons in the brain of mice in PD model induced by MPTP.

All references mentioned in the present invention are incorporated herein by reference as if each of those references has been incorporated by reference individually. Although the description referred to particular embodiments, it will be clear to a person skilled in the art that the present invention may be practiced with variation of these specific details. Hence this invention should not be construed as limited to the embodiments set forth herein.

What is claimed is:

1. A method of treating or preventing Parkinson's disease, or treating stroke in a subject, comprising administering to the subject an effective amount of an IL-22 or a dimer or multimer thereof.

2. The method of claim 1, wherein the method comprises administering to the subject an effective amount of an IL-22 dimer, and wherein the IL-22 dimer has a structure represented by Formula I:

M1-L-M2         Formula I wherein,
M1 is a first monomer of IL-22,
M2 is a second monomer of IL-22,
L is a linker connecting the first monomer and the second monomer and disposed therebetween, and
wherein the IL-22 dimer retains the biological activity of IL-22 and has a serum half-life of longer than twice of that of either the first or the second monomer.

3. The method of claim 2, wherein the linker L is selected from the group consisting of:
   (i) a short peptide comprising 3 to 50 amino acids, and
   (ii) a polypeptide of Formula II:

—Z—Y—Z—          Formula II wherein,
Y is a carrier protein,
Z is nothing, or a short peptide comprising 1 to 30 amino acids, and
"-" is a chemical bond or a covalent bond.

4. The method of claim 2, wherein the first monomer and the second monomer are identical.

5. The method of claim 2, wherein the biological activity comprises:
   (a) activating STAT3 in neurons in vitro,
   (b) protecting neurons and reducing the volume of cerebral infarction after ischemic injury in vivo,
   (c) activating STAT3 in dopaminergic neurons or hippocampal neurons in vitro,
   (d) significantly inhibiting the loss of dopaminergic neurons in substantia nigra in animals of PD model in vivo, or
   (e) significantly reducing the apoptosis of neurons in hippocampus in animals of AD model in vivo.

6. The method of claim 3, wherein the carrier protein is albumin or Fc fragment of human IgG.

7. The method of claim 1, wherein the method comprises administering to the subject an effective amount of an IL-22 dimer, and wherein the IL-22 dimer is formed by two monomers, each monomer comprising an amino acid sequence selected from SEQ ID NOs: 2-5.

8. The method of claim 7, wherein the method is used for treating or preventing Parkinson's disease.

9. The method of claim 7, wherein the method is used for treating stroke.

10. The method of claim 1, wherein the method comprises administering to the subject an effective amount of an IL-22 dimer, wherein the IL-22 dimer is formed by two monomers, each monomer comprising IL-22 and an Fc fragment of human IgG.

11. The method of claim 10, wherein each of the monomer comprises amino acids 163-385 of SEQ ID NO:2.

12. The method of claim 11, wherein each of the monomer comprises amino acids 147-162 of SEQ ID NO:2.

13. The method of claim 11, wherein each of the monomer comprises the amino acid sequence of SEQ ID NO:2.

14. The method of claim 10, wherein the method is used for treating or preventing Parkinson's disease.

15. The method of claim 10, wherein the method is used for treating stroke.

16. The method of claim 1, wherein the subject is human.

17. The method of claim 1, wherein the method is used for treating or preventing Parkinson's disease.

18. The method of claim 1, wherein the method is used for treating stroke.

* * * * *

SEQUENCE LISTING

```
<160> NUMBER OF SEQ ID NOS: 7

<210> SEQ ID NO 1
<211> LENGTH: 308
<212> TYPE: PRT
<213> ORGANISM: Artificial Sequence
<220> FEATURE:
<223> OTHER INFORMATION: IL-22 dimer

<400> SEQUENCE: 1

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95
```

```
Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Gly Ser Gly Gly Ser Gly Gly Gly Ser Gly Gly Gly
145             150                 155                 160

Gly Ser Ala Pro Ile Ser Ser His Cys Arg Leu Asp Lys Ser Asn Phe
                165                 170                 175

Gln Gln Pro Tyr Ile Thr Asn Arg Thr Phe Met Leu Ala Lys Glu Ala
            180                 185                 190

Ser Leu Ala Asp Asn Asn Thr Asp Val Arg Leu Ile Gly Glu Lys Leu
        195                 200                 205

Phe His Gly Val Ser Met Ser Glu Arg Cys Tyr Leu Met Lys Gln Val
    210                 215                 220

Leu Asn Phe Thr Leu Glu Glu Val Leu Phe Pro Gln Ser Asp Arg Phe
225                 230                 235                 240

Gln Pro Tyr Met Gln Glu Val Val Pro Phe Leu Ala Arg Leu Ser Asn
                245                 250                 255

Arg Leu Ser Thr Cys His Ile Glu Gly Asp Asp Leu His Ile Gln Arg
                260                 265                 270

Asn Val Gln Lys Leu Lys Asp Thr Val Lys Lys Leu Gly Glu Ser Gly
            275                 280                 285

Glu Ile Lys Ala Ile Gly Glu Leu Asp Leu Leu Phe Met Ser Leu Arg
        290                 295                 300

Asn Ala Cys Ile
305

<210> SEQ ID NO 2
<211> LENGTH: 385
<212> TYPE: PRT
<213> ORGANISM: Artificial Sequence
<220> FEATURE:
<223> OTHER INFORMATION: IL-22 monomer with Fc fragment

<400> SEQUENCE: 2

Ala Pro Ile Ser Ser His Cys Arg Leu Asp Lys Ser Asn Phe Gln Gln
  1               5                  10                  15

Pro Tyr Ile Thr Asn Arg Thr Phe Met Leu Ala Lys Glu Ala Ser Leu
             20                  25                  30

Ala Asp Asn Asn Thr Asp Val Arg Leu Ile Gly Glu Lys Leu Phe His
         35                  40                  45

Gly Val Ser Met Ser Glu Arg Cys Tyr Leu Met Lys Gln Val Leu Asn
     50                  55                  60

Phe Thr Leu Glu Glu Val Leu Phe Pro Gln Ser Asp Arg Phe Gln Pro
 65                  70                  75                  80

Tyr Met Gln Glu Val Val Pro Phe Leu Ala Arg Leu Ser Asn Arg Leu
                 85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140
```

```
Cys Ile Gly Ser Gly Gly Ser Gly Gly Gly Ser Gly Gly Gly
145                 150                 155                 160

Gly Ser Val Glu Cys Pro Pro Cys Pro Ala Pro Val Ala Gly Pro
            165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
            195                 200                 205

Pro Glu Val Gln Phe Asn Trp Tyr Val Asp Gly Val Glu Val His Asn
            210                 215                 220

Ala Lys Thr Lys Pro Arg Glu Glu Gln Phe Asn Ser Thr Phe Arg Val
225                 230                 235                 240

Val Ser Val Leu Thr Val Val His Gln Asp Trp Leu Asn Gly Lys Glu
            245                 250                 255

Tyr Lys Cys Lys Val Ser Asn Lys Gly Leu Pro Ala Ser Ile Glu Lys
            260                 265                 270

Thr Ile Ser Lys Thr Lys Gly Gln Pro Arg Glu Pro Gln Val Tyr Thr
            275                 280                 285

Leu Pro Pro Ser Arg Glu Glu Met Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
            325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
            370                 375                 380

Lys
385

<210> SEQ ID NO 3
<211> LENGTH: 375
<212> TYPE: PRT
<213> ORGANISM: Artificial Sequence
<220> FEATURE:
<223> OTHER INFORMATION: IL-22 monomer with Fc fragment

<400> SEQUENCE: 3

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
            85                  90                  95

Ser Thr Cys His Ile Glu Gly Asp Asp Leu His Ile Gln Arg Asn Val
            100                 105                 110
```

```
Gln Lys Leu Lys Asp Thr Val Lys Leu Gly Ser Gly Glu Ile
            115                 120                 125

Lys Ala Ile Gly Glu Leu Asp Leu Leu Phe Met Ser Leu Arg Asn Ala
130                 135                 140

Cys Ile Ala Ser Thr Lys Gly Pro Val Glu Cys Pro Pro Cys Pro Ala
145                 150                 155                 160

Pro Pro Val Ala Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Gln Phe Asn Trp Tyr Val Asp
        195                 200                 205

Gly Val Glu Val His Asn Ala Lys Thr Lys Pro Arg Glu Glu Gln Phe
    210                 215                 220

Asn Ser Thr Phe Arg Val Val Ser Val Leu Thr Val Val His Gln Asp
225                 230                 235                 240

Trp Leu Asn Gly Lys Glu Tyr Lys Cys Lys Val Ser Asn Lys Gly Leu
                245                 250                 255

Pro Ala Ser Ile Glu Lys Thr Ile Ser Lys Thr Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Met Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 4
<211> LENGTH: 385
<212> TYPE: PRT
<213> ORGANISM: Artificial Sequence
<220> FEATURE:
<223> OTHER INFORMATION: IL-22 monomer with Fc fragment

<400> SEQUENCE: 4

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95
```

```
Cys Lys Val Ser Asn Lys Gly Leu Pro Ala Ser Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Gly
    210                 215                 220

Ser Gly Gly Gly Ser Gly Gly Gly Ser Gly Gly Gly Gly Ser Ala
225                 230                 235                 240

Pro Ile Ser Ser His Cys Arg Leu Asp Lys Ser Asn Phe Gln Gln Pro
                245                 250                 255

Tyr Ile Thr Asn Arg Thr Phe Met Leu Ala Lys Glu Ala Ser Leu Ala
            260                 265                 270

Asp Asn Asn Thr Asp Val Arg Leu Ile Gly Glu Lys Leu Phe His Gly
        275                 280                 285

Val Ser Met Ser Glu Arg Cys Tyr Leu Met Lys Gln Val Leu Asn Phe
290                 295                 300

Thr Leu Glu Glu Val Leu Phe Pro Gln Ser Asp Arg Phe Gln Pro Tyr
305                 310                 315                 320

Met Gln Glu Val Val Pro Phe Leu Ala Arg Leu Ser Asn Arg Leu Ser
                325                 330                 335

Thr Cys His Ile Glu Gly Asp Asp Leu His Ile Gln Arg Asn Val Gln
            340                 345                 350

Lys Leu Lys Asp Thr Val Lys Lys Leu Gly Glu Ser Gly Glu Ile Lys
        355                 360                 365

Ala Ile Gly Glu Leu Asp Leu Leu Phe Met Ser Leu Arg Asn Ala Cys
    370                 375                 380

Ile
385

<210> SEQ ID NO 5
<211> LENGTH: 375
<212> TYPE: PRT
<213> ORGANISM: Artificial Sequence
<220> FEATURE:
<223> OTHER INFORMATION: IL-22 monomer with Fc fragment

<400> SEQUENCE: 5

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60
```

```
Thr Lys Pro Arg Glu Glu Gln Phe Asn Ser Thr Phe Arg Val Val Ser
 65                  70                  75                  80

Val Leu Thr Val Val His Gln Asp Trp Leu Asn Gly Lys Glu Tyr Lys
                 85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Ala
    210                 215                 220

Ser Thr Lys Gly Pro Ala Pro Ile Ser Ser His Cys Arg Leu Asp Lys
225                 230                 235                 240

Ser Asn Phe Gln Gln Pro Tyr Ile Thr Asn Arg Thr Phe Met Leu Ala
                245                 250                 255

Lys Glu Ala Ser Leu Ala Asp Asn Asn Thr Asp Val Arg Leu Ile Gly
            260                 265                 270

Glu Lys Leu Phe His Gly Val Ser Met Ser Glu Arg Cys Tyr Leu Met
        275                 280                 285

Lys Gln Val Leu Asn Phe Thr Leu Glu Glu Val Leu Phe Pro Gln Ser
    290                 295                 300

Asp Arg Phe Gln Pro Tyr Met Gln Glu Val Val Pro Phe Leu Ala Arg
305                 310                 315                 320

Leu Ser Asn Arg Leu Ser Thr Cys His Ile Glu Gly Asp Asp Leu His
                325                 330                 335

Ile Gln Arg Asn Val Gln Lys Leu Lys Asp Thr Val Lys Lys Leu Gly
            340                 345                 350

Glu Ser Gly Glu Ile Lys Ala Ile Gly Glu Leu Asp Leu Leu Phe Met
        355                 360                 365

Ser Leu Arg Asn Ala Cys Ile
    370                 375

<210> SEQ ID NO 6
<211> LENGTH: 1278
<212> TYPE: DNA
<213> ORGANISM: Artificial Sequence
<220> FEATURE:
<223> OTHER INFORMATION: DNA sequence encoding IL-22 monomer with Fc
      fragment

<400> SEQUENCE: 6
gaattcccca gacccatggc cgccctgcag aaatctgtga gctctttcct tatggggacc      60
ctggccacca gctgcctcct tctcttggcc ctcttggtac agggaggagc agctgcgccc     120
atcagctccc actgcaggct tgacaagtcc aacttccagc agccctatat caccaaccgc     180
accttcatgc tggctaagga ggctagcttg gctgataaca acacagacgt tcgtctcatt     240
```

| | |
|---|---|
| ggggagaaac tgttccacgg agtcagtatg agtgagcgct gctatctgat gaagcaggtg | 300 |
| ctgaacttca cccttgaaga agtgctgttc cctcaatctg ataggttcca gccttatatg | 360 |
| caggaggtgg tgcccttcct ggccaggctc agcaacaggc taagcacatg tcatattgaa | 420 |
| ggtgatgacc tgcatatcca gaggaatgtg caaaagctga aggacacagt gaaaaagctt | 480 |
| ggagagagtg gagagatcaa agcaattgga gaactggatt tgctgtttat gtctctgaga | 540 |
| aatgcctgca ttggatccgg tggcggttcc ggtggaggcg gaagcggcgg tggaggatca | 600 |
| gtcgagtgcc accgtgccc agcaccacct gtggcaggac cgtcagtctt cctcttcccc | 660 |
| ccaaaaccca aggacaccct catgatctcc cggacccctg aggtcacgtg cgtggtggtg | 720 |
| gacgtgagcc acgaagaccc cgaggtccag ttcaactggt acgtggacgg cgtggaggtg | 780 |
| cataatgcca agacaaagcc acgggaggag cagttcaaca gcacgttccg tgtggtcagc | 840 |
| gtcctcaccg ttgtgcacca ggactggctg aacggcaagg agtacaagtg caaggtctcc | 900 |
| aacaaggcc tcccagcctc catcgagaaa accatctcca aaccaaagg gcagccccga | 960 |
| gaaccacagg tgtacaccct gcccccatcc cgggaggaga tgaccaagaa ccaggtcagc | 1020 |
| ctgacctgcc tggtcaaagg cttctacccc agcgacatcg ccgtggagtg ggagagcaat | 1080 |
| gggcagccgg agaacaacta caagaccaca cctcccatgc tggactccga cggctccttc | 1140 |
| ttcctctaca gcaagctcac cgtggacaag agcaggtggc agcagggaa cgtcttctca | 1200 |
| tgctccgtga tgcatgaggc tctgcacaac cactacacgc agaagagcct ctccctgtct | 1260 |
| ccgggtaaat gatctaga | 1278 |

<210> SEQ ID NO 7
<211> LENGTH: 1248
<212> TYPE: DNA
<213> ORGANISM: Artificial Sequence
<220> FEATURE:
<223> OTHER INFORMATION: DNA sequence encoding IL-22 monomer with Fc fragment

<400> SEQUENCE: 7

| | |
|---|---|
| gaattcccca gacccatggc cgccctgcag aaatctgtga gctcttcct tatggggacc | 60 |
| ctggccacca gctgcctcct tctccttggcc ctcttggtac agggaggagc agctgcgccc | 120 |
| atcagctccc actgcaggct tgacaagtcc aacttccagc agcccatata caccaaccgc | 180 |
| acccttcatgc tggctaagga ggctagcttg gctgataaca acacagacgt tcgtctcatt | 240 |
| ggggagaaac tgttccacgg agtcagtatg agtgagcgct gctatctgat gaagcaggtg | 300 |
| ctgaacttca cccttgaaga agtgctgttc cctcaatctg ataggttcca gccttatatg | 360 |
| caggaggtgg tgcccttcct ggccaggctc agcaacaggc taagcacatg tcatattgaa | 420 |
| ggtgatgacc tgcatatcca gaggaatgtg caaaagctga aggacacagt gaaaaagctt | 480 |
| ggagagagtg gagagatcaa agcaattgga gaactggatt tgctgtttat gtctctgaga | 540 |
| aatgcctgca ttgccagcac aaagggacca gtcgagtgcc accgtgccc agcaccacct | 600 |
| gtggcaggac cgtcagtctt cctcttcccc ccaaaaccca aggacaccct catgatctcc | 660 |
| cggacccctg aggtcacgtg cgtggtggtg gacgtgagcc acgaagaccc cgaggtccag | 720 |
| ttcaactggt acgtggacgg cgtggaggtg cataatgcca agacaaagcc acgggaggag | 780 |
| cagttcaaca gcacgttccg tgtggtcagc gtcctcaccg ttgtgcacca ggactggctg | 840 |
| aacggcaagg agtacaagtg caaggtctcc aacaaggcc tcccagcctc catcgagaaa | 900 |
| accatctcca aaccaaagg gcagccccga gaaccacagg tgtacaccct gcccccatcc | 960 |

```
                                                       -continued cgggaggaga tgaccaagaa ccaggtcagc ctgacctgcc tggtcaaagg cttctacccc    1020
agcgacatcg ccgtggagtg ggagagcaat gggcagccgg agaacaacta caagaccaca    1080
cctcccatgc tggactccga cggctccttc ttcctctaca gcaagctcac cgtggacaag    1140
agcaggtggc agcaggggaa cgtcttctca tgctccgtga tgcatgaggc tctgcacaac    1200
cactacacgc agaagagcct ctccctgtct ccgggtaaat gatctaga                 1248
```